(12) United States Patent
Lynn et al.

(10) Patent No.: US 8,815,605 B2
(45) Date of Patent: Aug. 26, 2014

(54) METHODS AND KITS FOR QUANTITATIVE DETERMINATION OF TOTAL ORGANIC ACID CONTENT IN A COOLANT

(75) Inventors: Theodore B. Lynn, Hamden, CT (US); Timothy D. Lynn, Hamden, CT (US)

(73) Assignee: Dexsil Corporation, Hamden, CT (US)

( * ) Notice: Subject to any disclaimer, the term of this patent is extended or adjusted under 35 U.S.C. 154(b) by 0 days.

(21) Appl. No.: 13/451,242

(22) Filed: Apr. 19, 2012

(65) Prior Publication Data

US 2012/0301970 A1 Nov. 29, 2012

Related U.S. Application Data

(60) Provisional application No. 61/476,844, filed on Apr. 19, 2011.

(51) Int. Cl.
*G01N 21/79* (2006.01)
*G01N 21/78* (2006.01)

(52) U.S. Cl.
USPC ............ 436/129; 436/128; 436/127

(58) Field of Classification Search
CPC ....... G01N 21/79; G01N 21/78; G01N 12/00; G01N 33/52; G01N 33/00
USPC .......................... 436/129, 128, 127
See application file for complete search history.

(56) References Cited

U.S. PATENT DOCUMENTS

| | | |
|---|---|---|
| 4,894,346 A | 1/1990 | Myers et al. |
| 5,952,233 A | 9/1999 | Pellet et al. |
| 6,495,372 B1 | 12/2002 | Maes et al. |
| 2008/0019873 A1 | 1/2008 | Shah et al. |

FOREIGN PATENT DOCUMENTS

WO 2010075025 A2 7/2010

*Primary Examiner* — Christine T Mui
(74) *Attorney, Agent, or Firm* — Finch & Maloney PLLC

(57) ABSTRACT

The invention relates to methods and kits for determining the total organic acid content in a coolant sample.

3 Claims, 8 Drawing Sheets

METHODS AND KITS FOR QUANTITATIVE DETERMINATION OF TOTAL ORGANIC ACID CONTENT IN A COOLANT

This application claims the benefit of and priority to U.S. Provisional Application No. 61/476,844, filed on Apr. 19, 2011, which is herein incorporated by reference in its entirety.

FIELD OF THE INVENTION

The invention relates, in part, to methods and kits for determining the level of an organic acid in an aqueous coolant sample. Methods and kits of the invention, in part, may include steps such as contacting an organic acid in a coolant with an inorganic acid to protonate the organic acid, solvating the protonated organic acid, contacting the protonated organic acid with a reactant species, and detecting consumption of the reactant species to determine the organic acid content in the coolant.

BACKGROUND

Extended Life Coolants (ELCs) for internal combustion engines are based on Organic Acid Technology (OAT) and include an organic acid and other ingredients such as potassium hydroxide, ethylene or propylene glycols, water, etc. Recently OAT based coolants have been replacing silicate based coolants because of the longer service life of the OAT corrosion inhibitors. Unlike silicate based inhibitors, OAT inhibitors typically do not deplete over the 150,000 mile/5 year service interval. Most manufacturers emphasize the low to no maintenance feature of OAT coolants. Over the life of the coolant, the organic acids in ELCs can become depleted or compromised due to "topping off" with water or conventional (silicate based) coolant, and for optimal ELC performance and engine protection, it is important to maintain the total organic acid content of the ELC within a particular performance range. Replacing an ELC when it is still in an acceptable performance range can result in unnecessary costs, and failing to replace an ELC that is no longer within an acceptable performance range can lead to engine damage and lost productivity.

To avoid damage to engines and devices that results from contamination or dilution of an ELC, it is useful to be able to determine chemically the remaining organic acid content in the coolant to provide information on the coolant status.

SUMMARY OF THE INVENTION

According to an aspect of the invention, methods for identifying the quantity of a resident species present in a sample of an aqueous coolant are provided. The methods include steps of: (a) obtaining a coolant sample of a measured quantity, wherein the coolant is an aqueous coolant; (b) contacting the coolant sample with an inorganic acid to protonate a resident species contained in the coolant sample; (c) mixing the contacted coolant sample of (b) with a quantity of an organic extraction solvent in which the protonated resident species is soluble, solubilizing the protonated resident species in the organic extraction solvent, and allowing the resulting mixture to separate into phases that include at least an organic layer; (d) contacting the protonated resident species of a portion of the organic layer with an indicator and with a reactant species that will react with the protonated resident species, and reacting the protonated resident species, if any, thereby consuming a quantity of the reactant species commensurate with the quantity of the protonated resident species that was present in the coolant sample; and (e) determining the reactant species content as a measure of the resident species content of the coolant sample. In some embodiments, the resident species is an organic acidic species, the reactant species is a basic species, and the content of the resident species in the coolant sample may be expressed as the total organic acid content. In some embodiments, the reactant species is sodium hydroxide or potassium hydroxide. In certain embodiments, the resident species is an organic acid. In some embodiments, the organic acid is a short chain carboxylic or dicarboxylic acid up to C10. In some embodiments, the organic acid is an aromatic carboxylic or polycarboxylic acid. In certain embodiments, the carboxylic acid is 2-ethylhexanoic acid (EHA), benzoic acid, neodecanoic acid, or sebacic acid. In some embodiments, the inorganic acid is a mineral acid. In some embodiments, the inorganic acid is hydrochloric acid, nitric acid, sulfuric acid, phosphoric acid, or perchloric acid. In some embodiments, the organic extraction solvent is an organic extraction solvent that does not mix with water. In certain embodiments, the organic extraction solvent is an organic extraction solvent that does not entrain water. In some embodiments, the organic extraction solvent is iso-octane, mineral spirits, PA7 Thinner, HISOL #10, Aromatic 100, HISOL #15, Aromatic 150, butyl diglyme or mixtures thereof. In some embodiments, the coolant is an Extended Life Coolant [organic acid technology coolant (OAT)]. In certain embodiments, the step of contacting the protonated resident species of a portion of the organic layer with an indicator and with a reactant species that will react with the protonated resident species, and reacting the protonated resident species, if any, thereby consuming a quantity of the reactant species commensurate with the quantity of the protonated resident species that was present in the coolant sample, includes mixing the reactant species with the indicator prior to contacting the protonated resident species in the portion of the organic layer with the reactant species.

In some embodiments, determining the reactant species content as a measure of the resident species content of the coolant sample includes monitoring the indicator in the organic layer after contact with the reactant species/indicator mixture to determine whether the resident species in the coolant sample is above or below a predetermined level. In some embodiments, the step of contacting the protonated resident species of a portion of the organic layer with an indicator and with a reactant species that will react with the protonated resident species, and reacting the protonated resident species, if any, thereby consuming a quantity of the reactant species commensurate with the quantity of the protonated resident species that was present in the coolant sample, additionally includes mixing the protonated resident species from the portion of the organic layer with an aqueous reactant species and indicator, wherein the unreacted reactant species and the indicator form an aqueous layer distinct from the organic layer. In certain embodiments, determining the reactant species content as a measure of the resident species content of the coolant sample includes monitoring the indicator in the aqueous phase to determine whether the resident species in the coolant sample is above or below a predetermined level. In some embodiments, the step of contacting the protonated resident species of a portion of the organic layer with an indicator and with a reactant species that will react with the protonated resident species, and reacting the protonated resident species, if any, thereby consuming a quantity of the reactant species commensurate with the quantity of the protonated resident species that was present in the coolant sample, includes mixing the reactant species with the indicator and contacting the resulting mixture with an amount of the organic layer sufficient to change the indicator status. In some embodiments, determining the reactant species content as a measure of the resident species content of the coolant sample includes determining the amount of the organic layer sufficient to change the indicator status as a measure of the resident species content of the coolant sample. In certain embodiments, the step of contacting the protonated resident species of a portion of the organic layer with an indicator and with a reactant species that will react with the protonated resident species, and reacting the protonated resident species, if any, thereby consuming a quantity of the reactant species commensurate with the quantity of the protonated resident species that was present in the coolant sample includes i) drawing the portion of the organic layer into a graduated container; ii) expelling the portion drop wise into the indicator and reactant species mixture until the indicator status changes to indicate that the indicator endpoint is reached; and iii) determining the resident species content from the amount of the organic layer needed to reach the indicator endpoint. In some embodiments, the indicator and reactant species are provided in separate frangible ampules in a container and are mixed by squeezing the container from the exterior thereof, thereby crushing of the frangible ampules contained therein to release their contents within the container. In some embodiments, the step of contacting the protonated resident species of a portion of the organic layer with an indicator and with a reactant species that will react with the protonated resident species, and reacting the protonated resident species, if any, thereby consuming a quantity of the reactant species commensurate with the quantity of the protonated resident species that was present in the coolant sample includes mixing a measured portion of the organic layer with the indicator; and adding the reactant species to the resulting mixture in an amount sufficient to change the indicator status. In some embodiments, determining the reactant species content as a measure of the resident species content of the coolant sample includes determining the amount of the reactant species sufficient to change the indicator status as a measure of the resident species content of the coolant sample.

In certain embodiments, the step of contacting the protonated resident species of a portion of the organic layer with an indicator and with a reactant species that will react with the protonated resident species, and reacting the protonated resident species, if any, thereby consuming a quantity of the reactant species commensurate with the quantity of the protonated resident species that was present in the coolant sample includes i) mixing a measured portion of the organic layer with the indicator; ii) titrating the mixture of (i) with the reactant species in a graduated container until the indicator status changes to indicate that the titration indicator end point is reached; and iii) determining the amount reactant species titrated as a measure of the resident species content of the coolant sample. In some embodiments, the change in the indicator status results in a color change. In some embodiments, the indicator is a pH indicator. In some embodiments, the indicator is phenol red, thymol blue, cresol red, bromophenol red, or bromocresol green.

According to another aspect of the invention, methods for identifying the quantity of a resident species present in a sample of an aqueous coolant are provided. The methods include steps of: (a) obtaining a coolant sample of a measured quantity, wherein the coolant is an aqueous coolant; (b) contacting the coolant sample with an inorganic acid, to protonate a resident species contained in the coolant sample; (c) mixing the contacted coolant sample of (b) with a quantity of an organic extraction solvent in which the protonated resident species is soluble, solubilizing the protonated resident species in the organic extraction solvent, and allowing the resulting mixture to separate into phases that include at least an organic layer; (d) removing a portion of the organic layer and contacting the protonated resident species with a reactant species that will react with the protonated resident species, and reacting the protonated resident species, if any, thereby consuming a quantity of the reactant species commensurate with the quantity of the protonated resident species that was present in the coolant sample; (e) extracting the unreacted reactant species from at least a portion of the organic layer in (d) into an aqueous phase, wherein the extraction includes contacting the reactant species with a quantity of an aqueous extractant in which the reactant species is soluble but that is immiscible with the organic extraction solvent; (f) removing a portion of the aqueous phase containing the remaining reactant species and contacting the reactant species in the extracted aqueous phase with an indicator; and (g) determining the reactant species content as a measure of the resident species content of the coolant sample.

In certain embodiments, the reactant species is sodium hydroxide or potassium hydroxide. In some embodiments, the resident species is an organic acid. In some embodiments, the organic acid is a short chain carboxylic or dicarboxylic acid up to C10. In certain embodiments, the organic acid is an aromatic carboxylic acid. In some embodiments, the carboxylic acid is 2-ethylhexanoic acid (EHA), benzoic acid, neodecanoic acid, or sebacic acid. In some embodiments, the inorganic acid is a mineral acid. In some embodiments, the inorganic acid is hydrochloric acid, nitric acid, sulfuric acid, phosphoric acid, or perchloric acid. In certain embodiments, the organic extraction solvent is an organic extraction solvent that does not mix with water. In some embodiments, the organic extraction solvent is an organic extraction solvent that does not entrain water. Examples of suitable solvents include non-polar solvents and co-solvents such as aliphatic and aromatic hydrocarbons, naphthenic aromatic solvents and high flash solvents. In some embodiments, the organic extraction solvent is iso-octane, mineral spirits, PA7 Thinner, HISOL #10, Aromatic 100, HISOL #15, Aromatic 150, butyl diglyme or mixtures thereof. In certain embodiments, the coolant is an Extended Life Coolant [organic acid technology coolant (OAT)]. In some embodiments, determining the reactant species content as a measure of the resident species content of the coolant sample includes (i) adding an indicator to at least a portion of the aqueous extractant phase; (ii) titrating the aqueous extractant phase with a titration liquid contained in a first titration container bearing graduations to indicate the total volume of titration liquid expelled therefrom, the titration liquid containing a quantity of resident species equivalent which is selected relative to the volume of the coolant sample so that the titer indicated by the graduations is the total organic acid content of the coolant sample, the titration being carried out by expelling the titration liquid into the aqueous extractant phase until the indicator changes to indicate the endpoint of the titration, and thereupon ceasing to expel titration liquid from the first titration container and retaining the remaining titration liquid within the first titration container; and (iii) reading the graduations at the endpoint of the titration to determine the total volume of titration liquid expelled, and thereby the total organic acid content of the coolant sample. In some embodiments, extracting the unreacted reactant species from at least a portion of the organic layer into an aqueous phase, also includes separating the aqueous extractant from the organic extraction solvent to thereby provide an aqueous extractant phase containing reactant species, if any, extracted from the organic extraction solvent. In some embodiments, separating the aqueous extractant from contact with the solvent phase includes transferring the aqueous extractant to a second titration container, and wherein the first titration container includes a cap member dimensioned and configured to act as a closure that seals the second titration container while admitting the titration liquid therein, and a spout for admitting the titration liquid, the spout being directed into the second titration container when the cap member is in place as a closure for the second titration container, the method also including securing the first titration container to the second titration container before performing the titration and shaking the second titration container while admitting titration liquid therein. In certain embodiments, the resident species is an organic acidic species, the titration liquid is an acidic titration liquid and the titer indicated by the graduations on the first titration container is the total organic acid content of the coolant sample. In some embodiments, the indicator is a pH indicator. In some embodiments, the indicator is phenol red, thymol blue, cresol red, bromophenol red, or bromocresol green.

According to yet another aspect of the invention, kits for measuring the quantity of a resident species present in a sample of coolant are provided. The kits include (a) a first-sampling means for drawing a measured quantity of a coolant sample and introducing the measured sample into a container system; (b) a container system that includes (i) a first container that includes a measured quantity of an inorganic acid and an organic extraction solvent, (ii) a second container that includes one or more of a reactant species and an indicator; (c) a second-sampling means; (d) optionally, a titration means; and (e) instructions for using the kit to measure the quantity of the resident species in a sample of the coolant. In some embodiments, each container has a closable mouth dimensioned and configured to receive materials therethrough. In some embodiments, the first-sampling means is a first syringe and the second-sampling means is a second syringe. In certain embodiments, one or more syringe is a graduated syringe. In some embodiments, one or more syringe comprises a titration liquid. In some embodiments, one or more of the first and second syringes is dimensioned and configured to expel a titration liquid in a controlled stream therefrom and optionally comprises graduations thereon to indicate the total amount of titration liquid expelled from the syringe. In certain embodiments, the first-sampling means and the second-sampling means are graduated containers. In some embodiments, the graduated containers are syringes. In some embodiments, each graduated container includes a titration liquid. In some embodiments, the syringe is dimensioned and configured to expel a titration liquid in a controlled stream therefrom and optionally includes graduations thereon to indicate the total amount of titration liquid expelled from the syringe. In certain embodiments, the kit is dimensioned and configured to determine the amount of acidic species contained in the coolant sample. In some embodiments, the graduations on the syringe include a scale of total organic acid content. In some embodiments, at least one of the reactants contained in the first container is contained within a frangible ampule in the container. In some embodiments, the first container is sufficiently resilient to enable crushing of the frangible ampule contained therein to release their contents within the container by squeezing the container from the exterior thereof.

In certain embodiments, at least one of the reactants contained in the second container is contained within a frangible ampule in the container. In some embodiments, the second container is sufficiently resilient to enable crushing of the frangible ampule contained therein to release their contents within the container by squeezing the container from the exterior thereof. In some embodiments, (a) the first sampling means is a syringe configured to contain a predetermined amount of coolant sample, (b) the first container includes an inorganic acid and an organic extraction solvent; (c) the second sampling means is a syringe configured to collect a predetermined amount of an organic solvent extract; and (d) the second container includes an organic base and an indicator. In some embodiments, (a) the first sampling means is a syringe configured to contain a predetermined amount of coolant sample; (b) the first container includes an inorganic acid and an organic extraction solvent; (c) the second sampling means is a syringe configured to collect a predetermined amount of an organic solvent extract; and (d) the second container includes an aqueous base and an indicator. In certain embodiments, (a) the first sampling means is a syringe configured to collect a predetermined amount of coolant sample; (b) the first container includes an inorganic acid and an organic extraction solvent; (c) the second sampling means is a syringe configured to contain a predetermined amount of an organic solvent extract and including gradations to indicate the amount of the organic solvent extract expelled at the endpoint of a titration and calibrated to indicate the acid content in the coolant sample; and (d) the second container includes a base and an indicator. In some embodiments, the kit also includes a titration means, the titration means including an aqueous base and including gradations calibrated to indicate the acid content of the coolant sample; and wherein (a) the first sampling means is a syringe configured to contain a predetermined amount of coolant sample; (b) the first container includes an inorganic acid and an organic extraction solvent; (c) the second sampling means is a syringe configured to collect a predetermined amount of an organic solvent extract; and (d) the second container includes an indicator. In some embodiments, the reactant species is a basic species. In some embodiments, the basic species is an aqueous basic species. In certain embodiments, the basic species is sodium hydroxide or potassium hydroxide. In some embodiments, the basic species is an organic basic species. In some embodiments, the organic basic species includes alcoholic potassium hydroxide or isopropyl potassium hydroxide. In some embodiments, the inorganic acid is a mineral acid. In certain embodiments, the inorganic acid is hydrochloric acid, nitric acid, sulfuric acid, or perchloric acid. In some embodiments, the organic extraction solvent is an organic extraction solvent that does not mix with water. In some embodiments, the organic extraction solvent is an organic extraction solvent that does not entrain water. In certain embodiments, the organic extraction solvent is iso-octane, mineral spirits, PA7 Thinner, HISOL #10, Aromatic 100, HISOL #15, Aromatic 150, butyl diglyme or mixtures thereof. In some embodiments, the coolant is an Extended Life Coolant [organic acid technology coolant (OAT)]. In some embodiments, the resident species is an organic acid. In certain embodiments, the organic acid is a short chain carboxylic or dicarboxylic acid up to C10. In some embodiments, the organic acid is an aromatic carboxylic acid. In some embodiments, the carboxylic acid is 2-ethylhexanoic acid (EHA), benzoic acid, neodecanoic acid, or sebacic acid. In some embodiments, the indicator is a pH indicator. In certain embodiments, the indicator is phenol red, thymol blue, cresol red, bromophenol red, or bromocresol green.

In another aspect, method for identifying the quantity of a resident species present in a sample of an aqueous coolant is provided, the method comprising the steps of (a) obtaining a coolant sample of a measured quantity, wherein the coolant is an aqueous coolant, (b) contacting the coolant sample with an inorganic acid to protonate a resident species contained in the coolant sample, (c) mixing the contacted coolant sample of (b) with a quantity of an organic extraction solvent in which the protonated resident species is soluble, solubilizing the protonated resident species in the organic extraction solvent, and allowing the resulting mixture to separate into phases comprising at least an organic layer, (d) contacting the protonated resident species of a portion of the organic layer with a solid phase pH indicator, and (e) observing a color change in the solid phase pH indicator, the color change indicative of a threshold amount or a quantitative amount of the resident species in the aqueous coolant. The solid phase may include a pH indicator material in a neutral, basic or acidic state. The indicator may be, for example, bromothymol blue. The indicator may be on a porous substrate that is capable of wicking a solvent that includes an organic acid. The solid phase indicator may be placed into the solvent, allowing the solvent to advance upward through the solid phase indicator. The amount of indicator that changes color can be an indication of the amount of organic acid in the solvent. This can be used to quantify the amount of organic acid in the original coolant sample. The solid phase indicator can be laminated in a protective sheath or otherwise protected from environmental degradation. A kit can include the solid phase indicator as well as instructions and the additional components necessary for performing the case.

DETAILED DESCRIPTION

Figure 1:
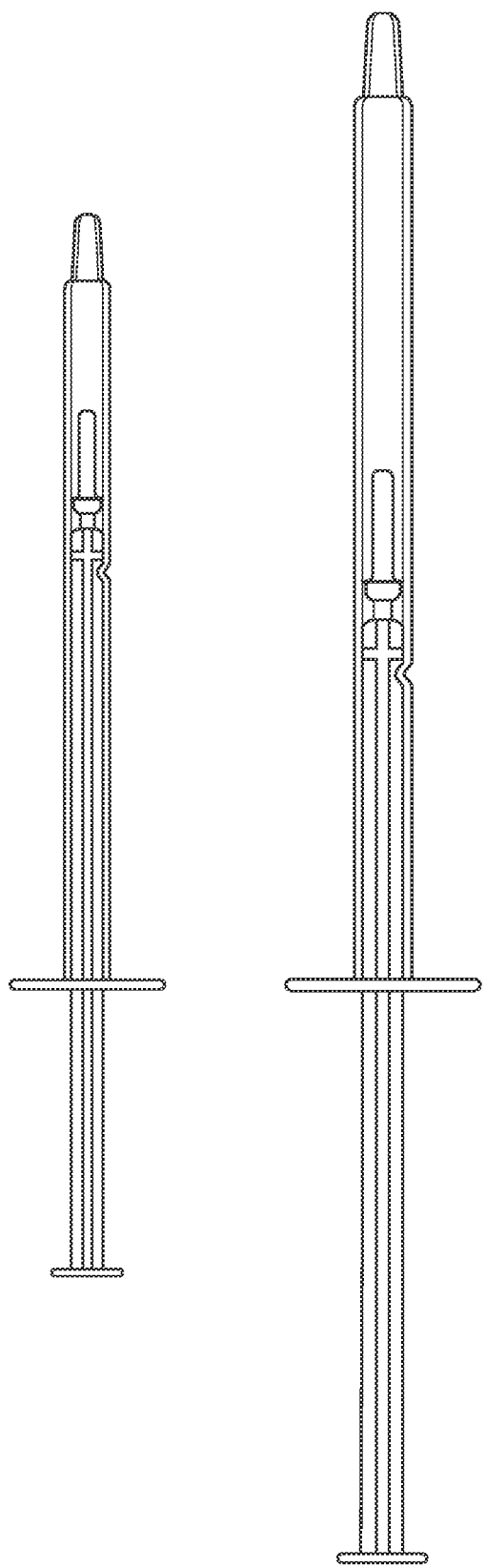
FIG. 1 shows two syringes with "stops" in the barrel that allow the plunger to be drawn back to a preset distance thus allowing a predetermined volume of liquid to be drawn up into the syringe. The syringe on the left has a stop at a position that permits a smaller volume of liquid to be drawn up as compared to the syringe on the right that has a stop at a higher level in its barrel.

Extended-life coolants (ELC) work with organic acid technology (OAT) and provide a number of benefits compared with conventional coolants. ELC can improve engine heat transfer and because ELCs are less abrasive than conventional silicate-based coolants, ELCs can result in less risk of engine wear and provide better engine protection. To maintain the engine protection provided by an ELC, it is important that the coolant not be excessively diluted, through "topping off" with non-ELCs or through other practices that alter the concentration of the OAT coolant. For example, diluting an ELC with an amount of a conventional coolant that is up to 20%, 25% or 30% of the ELC volume, may lead to extreme engine corrosion and result in costly repairs. Similarly, topping off, or diluting an ELC with water may alter the concentrations of an ELC substituent, such as the organic acid, and thus can compromise the engine protection provided by the ELC. As the organic acid content of an ELC decreases, the ELC's strength and effectiveness declines.

The organic acid content in an ELC can be determined using methods and kits of the invention. The determined value can be used to monitor the status of the ELC over time to determine whether the organic acid concentration is maintained in an appropriate range to effectively protect the engine. Use of methods of the invention to determine whether an ELC is in an appropriate organic acid content range can eliminate the need to replace an ELC at predetermined, and possibly overly conservative, time intervals. The easy-to-perform test method is also more likely to be implemented than existing techniques because it is less burdensome and time intensive.

Accordingly, it may be desirable to examine the condition of an OAT-based engine coolant periodically to determine whether the coolant maintains an adequate organic acid content or whether the content is inadequate and the ELC should be replaced or supplemented. Routine coolant testing is also part of many preventative maintenance protocols, which are used to verify the coolant condition. Prior methods of testing ELCs have included procedures that utilize A13 to precipitate the organic acid followed by the detection of excess A1 bound to an indicator to indicate an insufficient level of protection. An alternative to this complex test is laboratory testing, which requires expensive equipment, and is inconvenient and time consuming. Methods set forth herein provide an inexpensive and rapid testing alternative that provides information on the effective organic acid content of an ELC.

The present invention provides methods and kits for evaluating the organic acid content in a sample of an extended-life coolant (ELC). ELCs are coolants that are based on organic acid technology (OAT).

It has been identified that the organic acids used in ELC coolants are only sparingly soluble in water, if at all, unless they are in the ionic form, so if an inorganic acid is added to an ELC, the organic acid can be protonated and be forced out of aqueous solution. If the organic acid is then captured in a non-polar organic solvent, the amount of the organic acid can be directly detected, absent any interference from the aqueous-based coolant mixture. For instance, the organic acid can be rendered lipophilic so that it preferentially migrates to a non-aqueous phase from the aqueous coolant. Methods of the invention to determine the organic acid content of an ELC may include contacting an ELC sample with an excess of an inorganic acid that is suitable to protonate the organic acid in the coolant. Following protonation of the organic acid, the coolant sample can be contacted with an organic extraction solvent in which the protonated organic acid is soluble and the protonated acids can be transferred from the aqueous phase to the non-polar phase while the excess inorganic acid remains in the aqueous phase. The amount of the protonated organic acid can then be determined. The steps of protonating the organic acid and extracting the protonated organic acid into an organic solvent are elements that permit straightforward, economical methods of determining the organic acid content of an ELC, and thus allows for efficient determination of the status of an ELC.

In aspects of the invention, an ELC is an aqueous coolant that includes a resident species that is an organic acid species. Each coolant manufacturer sets their own standards for corrosion protection and acceptable levels of additives. Within a given manufacturer's coolant samples, the content of the organic acid species in the coolant sample may be expressed as the total organic acid content of the coolant and it can be expressed as a percent of the original organic acid content and strength of the ELC. For example, a 100% total organic acid content corresponds to full-strength ELC. Thus, a 100% strength ELC is an ELC at its manufactured strength, which would correspond to 100% organic acid content. Over time through dilution and contamination, ELC strength declines, reflecting a reduction in the organic acid content in the ELC. As used herein, the percentage of an ELC indicates the percent of the original content of organic acid that is present in the ELC. For example, an 80% ELC is an ELC that contains 80% of the organic acid content that was present in the original, 100%-strength ELC. Examples of test results that indicated organic acid content of various virgin, as-sold, ELCs are provided in Example 3. Tests of the strength of samples of various commercially available ELCs indicated that at 100% strength, various commercially available ELCs may have a weight percent of 2-ethylhexanoic acid (EHA) of at least 1.5%, 2%, 2.5%, or 3%.

Optimal performance by an ELC occurs at organic acid strength levels at which the coolant functions to control engine temperature and protect the engine from corrosion. Examples of acceptable strength levels in an ELC may include levels that are above 70%, 75%, 80%, 85%, 90%, 95%, 97%, 99%, up to 100% including all values in between each listed percent. With supplementation, it is possible that an ELC may have a strength that is greater than 100% of its original manufactured strength, and the organic acid content may be greater than 100% of its original manufactured level. Examples of unacceptable levels of organic acid in an ELC may be percentages of organic acid that are equal to or below 70% of the original percent of organic acid that was in the ELC. Acceptable levels may also vary with engine type and with specific engine applications. It will be understood that in some circumstances, an acceptable level can be set by the user based on the user's judgment and criteria. For example, in certain circumstances, an operator may not want to use coolant in which the organic acid content in an ELC is below 80% of the organic acid content in the original ELC and so in that circumstance, an acceptable level would be 80% and above, and an unacceptable level would be less than 80%. Those skilled in the art will understand how to determine a level (e.g. a predetermined level) such that methods of the invention provide a determination of whether a coolant has an acceptable or unacceptable level of organic acid. Using methods provided herein, one skilled in the art will be able to determine an acceptable level of organic acid in a coolant based on the user's criteria or circumstances and will understand how to set a predetermined level for use in the methods set forth herein.

For example, in some circumstances, it may be desirable to know whether the organic acid content in an ELC is above 70% (compared to the original organic acid content level), and the predetermined level in that case may be 70%. In some methods of the invention, a predetermined level can be an acceptable level of organic acid in a coolant sample. Non-limiting examples of methods of the invention include the use of direct and indirect pH titrations that may include an indicator, the results indicating different organic acid percentages in a coolant. The indicator may be a pH indicator such as a pH electrode, pH paper, or a colorimetric pH indicator. For example, in one exemplary, non-limiting embodiment of the invention thymol blue may be used as an indicator, and an organic acid content of 100% or 80% in a coolant can result in an indicator color of yellow. In the same exemplary embodiment, a coolant sample with only 70% organic acid content would result in a blue indicator color. The colors in this example can indicate whether the tested coolant has an acceptable or an unacceptable organic acid content, with a yellow color in this embodiment indicating an acceptable level of the organic acid content in the coolant, and a blue color indicating an unacceptable organic acid content in the coolant in this embodiment.

Similarly, in another non-limiting example, a method of the invention may include use of the indicator phenol red. In this example, an organic acid content of 100% in an ELC results in an indicator color of yellow, and an organic acid content of 80% results in an indicator color of orange, both of which are predetermined as acceptable levels. In contrast, in this example at 70% organic acid content, the indicator color is red, which indicates that the coolant has an unacceptably low organic acid content. The forgoing examples using thymol blue and phenol red as indicators are illustrative and non-limiting examples. It will be understood that other indicators can be used and that their associated colors will be indicative of organic acid content in methods of the invention. Those skilled in the art will understand how to use and interpret different indicators in methods of the invention and will be able to use methods set forth herein to determine levels and/or percentages of organic acids content in ELCs based on the indicator color changes.

A sample of coolant to be tested may be obtained in any convenient manner, for example, by drawing some coolant from an engine radiator into a suitable container such as a cup or can, and then using a suitable device, such as, a pipette, tube, or a sampling syringe, etc., to draw a measured quantity of the coolant. The sample may be measured volumetrically or by weight.

An organic acid species that can be tested for content in a coolant using methods and kits described herein can be a short chain carboxylic acid or dicarboxylic acid up to C10, as well as an aromatic mono, di, tri or tetracarboxylic acid. A coolant may include one or more types of organic acid. Suitable organic acid species will be known by those skilled in the art and may include, but are not limited to, aromatic carboxylic acids. The organic acid species may be soluble in glycol/water mixtures and can form a protective soap with exposed metals. Non-limiting examples of aromatic carboxylic acids that can be tested for using methods and kits of the invention include 2-ethylhexanoic acid (EHA), benzoic acid, neodecanoic acid, and sebacic acid.

According to methods of the invention, a sample of an ELC is obtained and an organic acid in the ELC is protonated by contacting the coolant sample with a strong acid. The strong acid may be, for example, an inorganic acid such as a mineral acid. The acid may have a pKa of less than 2, less than 0, or less than minus 2. Methods of the invention may include obtaining a measured sample of an ELC coolant and contacting the sample with an inorganic acid that is suitable to protonate the organic acid in the coolant. Non-limiting examples of inorganic acids that may be used in methods and kits of the invention to protonate an organic acid of a coolant include mineral acids and may include, but are not limited to hydrochloric acid, nitric acid, sulfuric acid, phosphoric acid, and perchloric acid. In some embodiments, more than 90%, more than 99%, or more than 99.9% of the organic acid is protonated.

Following protonation of the organic acid, the coolant sample is contacted with a quantity of an organic extraction solvent in which the protonated organic acid is preferentially soluble. The organic extraction solvent quantity may be a predetermined quantity of solvent, and the amount may be based on the amount of the coolant sample being tested. The contacting may comprise mixing using any suitable means. As used herein, the term "mixing" may include a mechanical mixing such as shaking, agitating, rocking, vortexing, stirring, etc. After mixing, the protonated organic acid and the organic extraction solvent mixture is allowed to separate into layers or phases. The separated mixture will include at least an organic layer (also referred to herein as an organic phase, or an organic solvent extract) that includes the protonated resident species, e.g. greater than 90, 95, or 99% of the protonated species.

In some embodiments of the invention, the organic extraction solvent is an organic extraction solvent that does not mix with water; or is an organic extraction solvent that does not entrain water. The extraction solvent may be easily separable from the coolant, may have a flash point of >140oC. Exemplary, but non-limiting examples of organic extraction solvents useful in methods and kits of the invention are any of the petroleum distillates and distillate mixtures from hexane to high flash mineral spirits including aromatic solvents from toluene to high flash aromatic mixtures, e.g., iso-octane, mineral spirits, butyl diglyme, PA7 Thinner, HISOL™ #10, Aromatic 100, HISOL #15, and Aromatic 150. Included in the acceptable solvents are substituted hydrocarbons including glycol ethers provided that they do not mix with water. Those skilled in the art will be aware of additional organic extraction solvents suitable for use in methods and kits of the invention.

According to methods of the invention, after the solvated, protonated organic acid mixture is allowed to separate, forming at least an organic layer (also referred to as an organic solvent extract), at least a portion of the organic layer from the separated mixture may be contacted with a reactant species that reacts with any protonated organic acid present in the organic layer portion. As used herein, the term "portion" means part of, or the entirety of (e.g. a full portion). A portion can be a measured portion. In methods and kits of the invention, the reactant species is a basic species, examples of which include, but are not limited to strong bases such as sodium hydroxide or potassium hydroxide. In methods of the invention, the amount of reactant species contacted with the portion of the organic layer may react with and consume an equivalent amount of the protonated organic acid species in the contacted portion of the organic layer.

Prior to contact, the portion or measured portion of the organic layer may be removed from the separated organic layer. Contacting the protonated organic acid species in the organic layer (or portion thereof) with the reactant species results in consumption of a quantity of the reactant species that is commensurate with the quantity of the protonated species that was present in the contacted portion of the organic layer. Thus, by determining the amount of the reactant species that remains (i.e., was not consumed) or determining the amount of the reactant species that was consumed, the amount of the organic acid that was present in the ELC sample can be determined. Some or all of the reactant species can react with and is consumed by the protonated organic acid species. The concentration of the organic acid in the ELC can be extrapolated from the amount of reactant species that was not consumed, or the level of reactant species that was consumed, when the reactant species is mixed with the extracted protonated organic acid. This extrapolation may also consider the ratio of solvent to coolant used as well as the efficiency of the transfer of the protonated organic species from the coolant to the organic solvent.

The portion or measured portion of the organic layer can also be contacted with an indicator, either before, concomitant with, or after the portion is contacted with the reactant species. The indicator can provide information on the amount of reactant species remaining in the organic layer portion, a value from which the organic acid content in the coolant can be extrapolated. In some embodiments of the invention, the indicator is a pH indicator, and may be a colorimetric pH indicator, with which the pH (or pH range) of a solution that includes the indicator is indicated by color. In some methods and kits of the invention, the pH indicator is phenol red, thymol blue, cresol red, bromophenol red, or bromocresol green. Additional examples of pH indicators that may be useful in methods or kits of the invention include, but are not limited to p-Naphtholbenzein, methyl red, bromocresol purple, bromophenol blue, Congo red, or chlorophenol red. Additional pH indicators suitable for determining the amount of a reactant species using methods and kits of the invention, and thus suitable to determine the organic acid content of an ELC will be known to those skilled in the art. It will be understood by those skilled in the art that pH can be determined in a method of the invention using a pH indicator, a pH electrode, a pH test strip, or any other suitable method of determining pH of a solution. Similarly, a kit of the invention may include a pH-determining means such as an indicator, a pH electrode, a pH test strip, and or a pH meter.

Following the combination of the reactant species with the protonated organic acid species, the content of the unconsumed reactant species may provide a measure of the organic acid content of the coolant sample. Determining the content of the reactant species can be performed using any suitable means, including determining the pH of the combination of the reactant species and the protonated organic acid species. The pH of the reacted mixture can be determined using a pH indicator as described herein. In some embodiments of the invention, the color change of the pH indicator in a solution is used to determine the amount of the reactant species. Those skilled in the art will recognize that the amount of reactant species remaining is inversely proportional to the amount of reactant species consumed. Thus, the amount of organic acid species can be determined either by ascertaining the amount of reactant species remaining or the amount of reactant species that has been consumed. Methods of the invention may include the use of a colorimetric pH indicator to determine the amount of reactant species remaining or consumed and thus the indicator can be used to determine the total organic acid content of the coolant.

In some embodiments of the invention, an indicator change (e.g. a color change) may provide information on whether a coolant is at an acceptable or unacceptable organic acid content. In certain embodiments of the invention, determining the organic acid content of an ELC may include a titration (e.g. a portion of the organic layer with a reactant species) to reach an endpoint, wherein the amount of the titration liquid required to reach the endpoint is indicative of the organic acid content of the coolant sample.

A colorimetric indicator can be used to determine whether the organic acid content in the coolant sample is above or below a predetermined level. Thus, by monitoring the color of the indicator, the content of the resident species (e.g. the organic acid content) in the coolant sample can be determined. For example, observing or recording the color of the mixture, one can determine whether the organic acid content is above or below a predetermined level in the coolant sample. As used herein, a predetermined level is a level that is selected based on criteria for an assay or test. A predetermined level may be an "acceptable" level for an organic acid content in a coolant tested. A coolant that meets or exceeds the acceptable level may support a decision that the coolant is satisfactory for engine use. In contrast, an organic acid content in a coolant that falls below the acceptable level may be considered unacceptable for continued use. Determining that a coolant has an unacceptable level may support a decision to replace or supplement the coolant.

In some embodiments of the invention, a pH indicator is added to the organic layer or to an extract of such layer to give a visual indication of the amount of the unconsumed reactant present. Alternatively, a pH meter or any other suitable instrument or technique to determine the unconsumed reactant content of the organic layer or extract from that layer could be employed. Liquid titration and use of a colorimetric pH indicator may provide a method suited for use in a field test kit, because titration and the color-change endpoint may be simpler for use by untrained personnel.

Various Test Embodiments

As described above, initial steps of methods of the invention may include contacting a coolant sample with a strong acid to protonate the organic acids present and contacting the protonated organic acids with an organic extraction solvent in which the protonated organic acid is soluble. The steps result in an organic layer that contains the protonated organic acid. After solubilizing the protonated organic acid, various strategies can be used to determine the qualitative or quantitative organic acid content of the coolant, a value that indicates the coolant strength. In methods of the invention, a sample of coolant can be obtained using any suitable means. Addition of reagents to the sample and mixing reagents with the sample in methods of the invention can also be performed using any suitable means.

Go/No Go Organic Extraction

One method of the invention includes contacting a coolant sample with an inorganic acid to protonate the organic acids and mixing the protonated organic acids with an organic extraction solvent in which the protonated organic acid is soluble, allowing the mixture to separate, which results in at least an organic layer. The method also includes mixing a reactant species with an indicator and contacting the protonated organic acid in a portion of the organic layer with the reactant species/indicator mixture. In such method, determining the reactant species content can include monitoring the indicator color in the organic layer after the organic layer portion has been contacted with the reactant species/indicator mixture. The color indicates whether the organic acid content in the coolant sample is above or below a predetermined level.

Go/No go Aqueous Extraction Method

A method of the invention may include monitoring an aqueous phase that includes unreacted (unconsumed) reactant species to determine the status of the organic acid in a coolant. In this method, a coolant sample is contacted with an inorganic acid to protonate the organic acids and the protonated organic acid is mixed with an organic extraction solvent in which the protonated organic acid is soluble, allowing the mixture to separate, which results in at least an organic layer separate from the aqueous coolant. This method of the invention also includes mixing the protonated organic acid species from a portion of the organic layer with an aqueous reactant species and an indicator. The mixing results in the unreacted reactant species and the indicator forming an aqueous layer that is distinct from the organic layer. The reactant species content can then be determined by monitoring the indicator in the aqueous phase to determine whether the resident species in the coolant sample is above or below a predetermined level. Thus, the color change in the aqueous phase may be monitored and a change of an indicator indicates the amount of remaining unreacted reactant species and therefore can be used to determine the amount of reactant species that was consumed. From the amount of reactant species consumed or the amount reacted (which can be derived from the amount remaining), the level of organic acid in the coolant sample can be determined.

Organic Layer Added Until Indicator Endpoint Reached

Another method of the invention includes contacting a coolant sample with an inorganic acid to protonate the organic acids and mixing the protonated organic acid with an organic extraction solvent in which the protonated organic acid is soluble, allowing the mixture to separate, which results in at least an organic layer. The method also includes mixing an indicator with a reactant species and then adding an amount of the organic layer to the indicator/reactant species mixture. The amount of the organic layer added is the amount sufficient to reach a predetermined endpoint. In some embodiments, the indicator is a colorimetric pH indicator and the endpoint is an indicator color change. The organic acid content present in the coolant determines the amount of the organic layer that needs to be added to reach the endpoint. Thus, by monitoring the amount of organic layer necessary to trigger the indicator color change, the organic acid content in the coolant can be determined.

Determining the organic acid content of the coolant includes determining the amount of the organic layer that is sufficient to change the indicator status, which provides a measure of the organic acid in the coolant. From the amount of organic layer added, the level of organic acid in the coolant sample can be determined using methods of the invention.

As will be understood by practitioners in the art, the amount of organic layer needed to add to the reactant species (e.g. base) and reach the titration endpoint is proportional to the concentration of the organic acid in the coolant. Thus, at the endpoint, the equivalents of reactant species (e.g. the base) equals the equivalents of organic acid added so equivalents of reactant species divided by the volume of organic layer equals the concentration in the extract multiplied by any dilution factor that results from reacting less than 100% of the organic phase.

A non-limiting, exemplary calculation to determine the amount or percentage of organic acid in an OAT coolant sample is as follows. For this calculation, X mL of coolant sample can be placed into a first container (e.g., Tube 1) along with Y mL of a solvent and an inorganic acid. The mixture is shaken, allowed to separate, and an aliquot (Z mL) of the organic layer is then removed and placed into a second container (e.g. Tube 2), where it is titrated with n mL of a base of concentration C. In some embodiments, an indicator is included in Tube 2, and the color change of the indicator can be observed as a measure of the status of the titration endpoint.

Calculations can be done as follows to determine the concentration of organic acid in the tested coolant sample and to determine the percentage of organic acid in the coolant sample versus the percentage of organic acid in the original 100% fresh coolant.

The concentration of organic acid in a coolant is equal to:

$$\frac{nC(Y/Z)}{X}$$

In some embodiments, a correction factor may be employed to compensate for extraction inefficiencies and the like. The above calculation provides the concentration of organic acid in the coolant. To determine the percentage of organic acid in the coolant, the value from above is divided by the concentration of organic acid in full strength coolant and then multiplied by 100.

In some embodiments of the invention, adding the organic layer to the combined indicator and reactant species may include drawing the portion of the organic layer into a graduated container (that may include volume indicia) and expelling the portion in a controlled manner (e.g., drop wise) into the indicator and reactant species mixture until the indicator status changes to indicate that the indicator endpoint is reached. When the endpoint is reached, the amount of organic layer that was needed to reach the endpoint can be determined as a measure of the resident species content of the coolant sample. The indicator, reactant species, and organic layer may be provided in any suitable containers, and in some embodiments, the indicator and reactant species are provided in separate frangible ampules in a container and are mixed by squeezing the container from the exterior thereof, thereby crushing the frangible ampules contained therein to release their contents within the container.

Organic Extract Added to Indicator First and Titrated with Base

Another aspect of the invention includes contacting a coolant sample with an inorganic acid to protonate the organic acid and mixing the protonated organic acid with an organic extraction solvent in which the protonated organic acid is soluble, and allowing the mixture to separate, which results in at least an organic layer. The organic layer can be separated from the aqueous layer with the excess acid. An indicator is mixed with the organic layer or portion thereof. The reactant species is then added to the organic layer/indicator mixture in an amount that is sufficient to change the indicator status. In some embodiments, the indicator is a colorimetric pH indicator, the change in indicator status is a change in the color in the mixture, and the color change indicates the endpoint of the amount of the reactant species needed. The amount of the reactant species sufficient to change the indicator status is a measure of the organic acid species content of the coolant sample. In some embodiments of the invention, the method includes mixing a measured portion of the organic layer with the indicator; titrating the resulting mixture with the reactant species in a graduated container until the indicator status changes to indicate that the titration indicator end point is reached; and determining the amount reactant species titrated as a measure of the organic acid content of the coolant sample.

Direct Reaction with a Solid Phase pH Indicator

In another aspect, a coolant extract may be directly reacted with a solid phase indicator to provide information regarding the presence and quantity of organic acids, e.g., EHA, in the coolant sample. Preferably after protonation, organic acids may be extracted directly from the coolant with an organic solvent or mixture of solvents. The extracted acids may then be contacted with a solid phase pH indicator which can change color depending on the amount of organic acid present. The color change may be quantitative or qualitative.

In one embodiment, a coolant sample is extracted with an organic solvent or co-solvent such as isooctane or a 25:75 v/v mixture of butyldiglyme and PA7. In this embodiment the coolant to solvent ratio may be, for example, 2:1 or 1:1 or 1:2 or 1:5 or any ratio within these ranges. A solid phase indicator can be prepared by applying a basic, alcoholic pH indicator solution to a solid, preferably porous, substrate such as filter paper or sintered polyethylene. The material is then dried prior to use. A limited number of pH indicators may be suitable as many common pH indicators may lose most or all of their color when allowed to air dry on a solid substrate. It has been found that bromothymol blue (BTB) is stable and maintains its color when applied at a high pH and allowed to dry on the solid substrate. Other examples of indicator materials that may be useful include Metacresol Purple, Curcumin, Neutral Red, Brilliant Yellow, Alizarin, Chlorophenol Red, Bromocresol Purple and Propyl Red. Some indicators, such as phenol red, thymol blue and cresol red may be difficult to incorporate into a dry system because they may lose a portion or all of their color when dried on a porous material such as filter paper. By applying the indicator at a high pH with a predetermined or calculable amount of hydroxyl ions, e.g., NaOH or KOH, the solid phase indicator can react with an acid as the sample is absorbed into, across or through the solid phase indicator. If the solid phase indicator is porous and at least partially lipophilic, the solvent containing the OAT acid can be drawn through the solid phase indicator, allowing any acid that is present to react with the hydroxyl ions that are present on the indicator strip. After neutralization past the transition point of the pH indicator, the presence of excess acid will change the color of the indicator from basic to acidic. As the solvent is drawn through the solid phase substrate, the solvent front advances through the solid phase. As long as there is excess acid (unreacted with the basic indicator material) in the solvent, the indicator will change color as the acid passes across a specific point on the solid phase indicator strip. However, once the acid in the solvent has been neutralized (loses a proton), the solvent front can advance along the strip without changing the color of the indicator. In this manner, the amount of acid in the sample can be quantitatively measured by determining how far along the solvent pathway the color change occurs in relation to the total distance traveled by the solvent. A solvent sample with a greater amount of acid will cause a change in indicator color over a greater percentage of the total distance traveled by the solvent.

The solid phase indicator may include both a solid substrate and a pH indicator. The solid substrate may be porous and may be partially or strongly lipophilic in order to draw the solvent sample along the substrate via capillary action, for example. The substrate may also be inert to organic solvents and should not be soluble in the solvents chosen for extracting the organic acids. Appropriate substrate materials may include, for example, paper, such as filter paper, woven and non-woven synthetics, and sintered or expanded polymers such as polyethylene, polypropylene and PTFE. The substrate may in the shape of a strip and may have a length greater than its width which is greater than its thickness. The indicator treated substrate (solid phase indicator) may be coated, sealed or laminated in a second material to improve shelf life of the indicator as well as to limit exposure to test solvent to a specific portion of the substrate. For example, a treated indicator strip may be laminated in a solvent impermeable sheath that excludes moisture and oxygen from contacting the strip. A single edge of the strip may be exposed through the laminating sheet. The edge may be exposed from the time the strip is laminated or the lamination may be cut prior to use. The exposed edge can be placed in the solvent sample and will be the interface through which the solvent is drawn into the solid phase indicator. Indicia may be printed on the solid phase indicator or on the laminating material. These indicia may reference, for example, a TAN value, an OAT rating or a stop line to indicate when the solid phase indicator should be removed from the solvent sample. The solid phase indicator (or coating) may also be marked with one or more colors to provide guidance to the user regarding a specific color change to look for.

Solid phase indicators can be made by saturating a porous substrate, such as acid free filter paper, with a solution of pH indicator and a base. The solvent used should be able to solubilize both the pH indicator and the base, and may also be volatile so that it quickly evaporates after application, leaving behind dry pH indicator in a basic form. For instance, if bromothymol blue (BTB) is used, the substrate can exhibit a blue or green color due to the presence of hydroxyl ions. Upon reaction with an acid, the substrate can turn yellow. The solvent can be an alcohol, including aliphatic alcohols such as methanol, ethanol, propanol or isopropanol. A base may be added to the solvent to produce a caustic or mildly caustic alcoholic solution. NaOH or KOH, for instance, can be added to produce solutions having NaOH or KOH concentrations of 0.001 to 0.1N, 0.01 to 0.05 N or 0.01 to 0.03 N. The pH indicator may be added at a concentration that provides the sharpest color change for the test. Appropriate concentrations in various embodiments have been shown to be, by weight, 0.01 to 0.5%, 0.05 to 0.5%, 0.01 to 0.03% and 0.01 to 0.02%. The solid substrate may be dipped into the alcoholic indicator solution or the solution may be quantitatively disposed on the substrate. The quantity of solution absorbed by the substrate can be measured by weight or volume to determine the amount of indicator and base on the solid phase indicator. Alternatively, the amount of solution disposed on the substrate can be measured volumetrically or by weight. After being allowed to dry, the solid phase indicator can be packaged, coated or laminated to protect the indicator from environmental degradation. In one set of embodiments, the solid phase indicator is heat laminated between two layers of ethylene-vinyl acetate (EVA). One edge (typically an end) of the solid phase indicator may be exposed so that when placed in the organic solvent the solid phase indicator can absorb the sample. In another embodiment the solid phase indicator may be completely sealed and the seal or lamination may be cut or otherwise opened prior to use.

Kits

The present invention also provides kits in which reagents necessary to carry out methods of the invention are conveniently premeasured and stored so that the user may release the reagents and carry out the methods without jeopardizing the accuracy of the test due to spillage, measuring errors and the like. Kits of the invention can be used to determine the status of a resident species in a coolant. Coolants that can be tested using a kit of the invention include Extended Life Coolants, which are also known as organic acid technology coolants (OAT). A kit of the invention can be used to determine the content of the resident species in an ELC and a resident species can be an organic acid species. Thus, kits of the invention can be used to determine the organic acid content of an ELC. Examples of organic acids that can be determined using a kit of the invention include, but are not limited to short chain carboxylic acids or dicarboxylic acids up to C10, as well as aromatic mono, di, tri and tetracarboxylic acids. Examples of carboxylic acids that may be determined using a kit of the invention include, but are not limited to, 2-ethylhexanoic acid (EHA), benzoic acid, neodecanoic acid, or sebacic acid.

Kits of the invention may include a variety of components and reagents. Kits may include zero, one, two, three or more sampling means for drawing a measured quantity of a coolant sample and introducing the measured sample into a container system. Any suitable sampling means and any suitable containers can be used and included in kits of the invention. Sampling means may include, but are not limited to pipettes, burettes, syringes, tubes, straws, and the like.

Kits of the invention may include zero, one, two, three or more containers, which may include, but are not limited to cans, jars, tubes, vials, bottles, etc. A container included in a kit of the invention may have a closable mouth that is dimensioned and configured to receive materials. A kit of the invention may include zero, one, two, three or more titration means. Examples of titration means include, but are not limited to, burettes, pipettes, syringes, tubes, and the like. Containers, sampling means, and titration means in kits of the invention may include indicia, including, but not limited to scales, numbers, and gradations that indicate volume or content. Such markings may be etched or may be in ink, etc. and may provide a means to determine a volume delivered from, or an amount contained in, the container, sampling means or titration means. A titration means or syringe bearing graduations that are scaled and numbered to indicate directly the total organic acid content of the coolant sample at the endpoint of the titration, are provided in some embodiments of the invention and can obviate the need for the user to perform any computations to interpret the results of the test. Kits of the invention may include sampling means that are graduated containers, which in some embodiments of the invention, may be syringes. In some kits of the invention, a graduated container includes a titration liquid. Kits of the invention may include one or more syringes that are dimensioned and configured to expel a titration liquid in a controlled stream and the one or more syringes may include graduations that indicate the total amount of titration liquid expelled from (or remaining in) the syringe. A syringe of a kit of the invention may include graduations on the syringe that include a scale of total organic acid content. Thus, in some embodiments, kits of the invention may include a container (e.g., a syringe) that includes gradations with a scale which is read out directly as a percent of full strength coolant or as a percent of full strength organic acid content of the coolant.

In some embodiments of the invention, a syringe useful to practice a method of the invention and/or to be included in a kit of the invention may include a syringe that has a "stop" in the barrel that allows the plunger to be pulled back only to a predetermined point in the barrel, thereby permitting a predetermined volume of fluid to be picked up by the syringe. Examples of such syringes can be seen in FIG. 1, which shows two syringes with different stop levels, as illustrated by the distance each plunger has been pulled back until it reaches the stop and cannot be pulled back further along the barrel.

Figure 2:
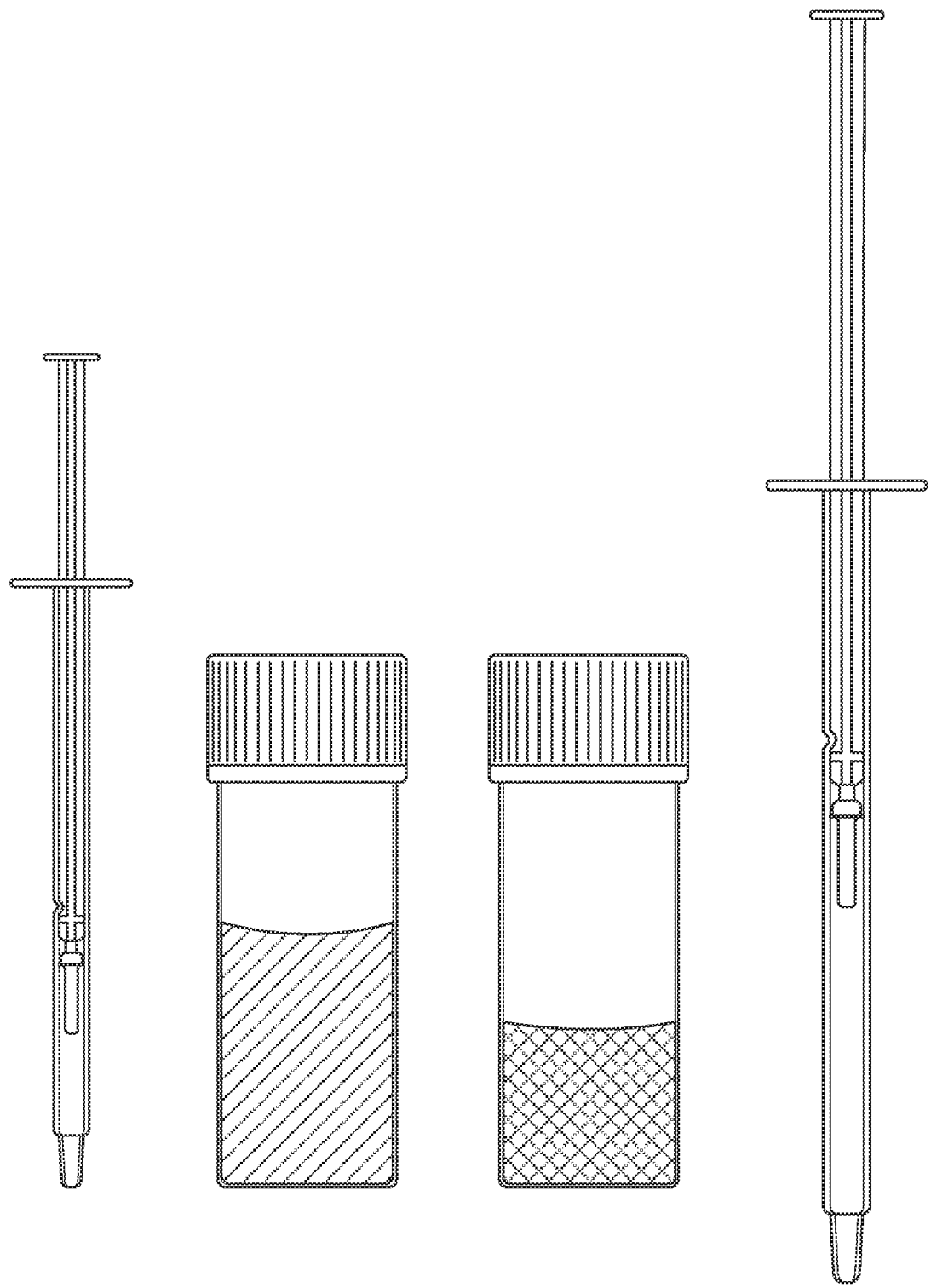
FIG. 2 shows an exemplary kit that includes two syringes with stops, and two vials. The leftmost vial, as shown, contains a premeasured amount of an organic solvent and inorganic acid and the rightmost vial, as shown, contains a predetermined amount of a reactant species (e.g. a base) and an indicator.

FIG. 2 shows components that may be useful in methods of the invention and may comprise a kit of the invention. FIG. 2 shows two syringes with different stop positions providing two different fixed volumes. An exemplary syringe on the left may be used to draw up a predetermined amount of a coolant sample and after the coolant sample has been mixed with the solvent and inorganic acid, and the mixture allowed to separate, the syringe on the right can be used to draw up a predetermined volume of organic layer that can be added to the reactant species (base) and an indicator. FIG. 2 also shows non-limiting examples of containers that can be used in methods and kits of the invention, including a container as shown on the left that contains solvent and inorganic acid and to which the OAT coolant sample can be added using the leftmost syringe. After the coolant, inorganic acid and solvent are mixed and allowed to separate, the rightmost syringe can be used to remove a predetermined amount of the organic layer, and to add that volume to a container such as the one illustrated on the right, which contains a reactant species (e.g. base) and an indicator. Additional, non-limiting, exemplary, containers can be used in methods and kits of the invention.

Kits of the invention may be dimensioned and configured in any manner suitable to determine the amount of acidic species contained in an ELC. A kit may include components such as containers, sampling means, titration means and reagents suitable for carrying out a method of the invention to determine the organic acid content of a coolant. A kit of the invention is readily usable by persons unskilled in laboratory analysis techniques and may be used in the field by untrained persons by simply following relatively simple (as compared to laboratory analyses) instructions. A kit of the invention may include instructions for use of the kit to determine the level of organic acid in a coolant.

Kits of the invention include reagents. Reagents included in a kit of the invention are an organic extraction solvent in which a resident species is soluble, and an inorganic acid. An inorganic acid may be a mineral acid, non-limiting examples of which are hydrochloric acid, nitric acid, sulfuric acid, and perchloric acid. An organic extraction solvent of a kit of the invention may be an organic extraction solvent that does not mix with water and/or does not entrain water. In some embodiments of the kit, an organic extraction solvent is iso-octane, mineral spirits, PA7 Thinner, HISOL #10, Aromatic 100, HISOL #15, Aromatic 150, butyl diglyme or mixtures thereof.

A kit may also include one or more additional reagents. One reagent in a kit of the invention may be a reactant species and the reactant species may be a basic species. A basic species of a kit may be an aqueous basic species, including, but not limited to, sodium hydroxide or potassium hydroxide. In some embodiments of the invention, a basic species in a kit is an organic basic species. Non-limiting examples of organic basic species that can be used in kits and methods of the invention include alcoholic potassium hydroxide and isopropyl potassium hydroxide.

A kit of the invention may also include one or more indicators. In some embodiments of the invention, an indicator is a pH indicator. A pH indicator may be a colorimetric indicator that indicates the pH status of a solution through a color change. For example, a solution that includes a colorimetric pH indicator may be red at a particular pH, and the color may change to blue or yellow at a higher or lower pH. The skilled artisan will recognize that different indicators are useful to detect different pH ranges, and that colors and color changes will depend on the indicator selected, its functional pH range, and the pH of the solution that includes the indicator. Some kits of the invention may include one or more pH indicators selected from phenol red, thymol blue, cresol red, bromophenol red, and bromocresol green. Additional examples of pH indicators that may be useful in methods or kits of the invention include, but are not limited to p-naphtholbenzein, methyl red, bromocresol purple, bromophenol blue, Congo red, or chlorophenol red. In some embodiments, the pH indicator may in the form of a solid phase indicator as described herein. The solid phase indicator may be laminated in a moisture/oxygen barrier material. The solid phase indicator may include indicia for targeting a solvent front end point as well as indicia for reading results. Instructions may include details on exposing a surface of the solid phase indicator to the solvent sample. Such details may include cutting the laminate. Additional pH indicators suitable for inclusion of kits of the invention will be known to those skilled in the art.

A kit of the invention may also include a color chart and/or colored samples that provide the pH and/or the organic acid content number of a coolant sample when the pH indicator in the sample attains a particular color shade. A kit of the invention may also include one or more control coolant aliquots, and/or a graduated series of control aliquots. A control coolant aliquot may include a known percentage or concentration of organic acid and can be tested in parallel with a coolant sample. Results from one or more control tests can be compared with the results from a coolant sample that is tested. For example, a control test may result in a specific color change that may then be compared to a test sample result to determine if the test sample is acceptable or unacceptable. Use of controls in a kit of the invention can provide a measure of the percentage or concentration of organic acid in the coolant sample through comparison with a known organic acid level a control aliquot. Controls that may be included in a kit of the invention may also comprise one or more containers containing liquids having a color to which the color result of a tested sample can be compared as a measure of the organic acid concentration or percentage in the tested sample. One skilled in the art will understand how to utilize various types of controls in the practice of methods of the invention.

Although methods of invention may be carried out by any suitable apparatus, including laboratory apparatus, one of its significant advantages is that it may be accurately carried out in a field test kit, which can be sufficiently inexpensive that it is economically feasible to use the kit once and then discard it. A suitable field test kit for carrying out the method of the invention may include prepackaged, premeasured reagents in accurately measured quantities, thereby facilitating the use of the test kit by inexperienced personnel with very little or no prior training Thus, some components of a kit of the invention may include premeasured reagents in a convenient package. For example, premeasured reagents may be provided in containers shown in FIG. 2, with inorganic acid and solvent as shown in the leftmost container, and a reactant species (e.g. base) and indicator as shown in the rightmost container. In some embodiments of the invention, a kit may have a reagent contained within a frangible ampule in a container. Such a container may be sufficiently resilient to enable crushing of the frangible ampule contained therein to release its contents within the container by squeezing the container from the exterior. Some kits also include a second container that contains a frangible ampule containing a reagent, and the second container is sufficiently resilient to enable crushing of the frangible ampule contained therein to release its contents within the container by squeezing the container from the exterior thereof. Some containers in kits of the invention contain two frangible ampules within a single container, each of which contains a different reagent, and each of which can be independently crushed to release its contents into the container by squeezing the container from the exterior.

Various embodiments of kits of the invention are envisioned, each permitting determination of the amount of an organic acid in a coolant. Examples of kits are described herein and are not intended to be limiting.

One exemplary kit includes a syringe as a first sampling means, and the syringe is configured to obtain and dispense a predetermined amount of coolant sample. The kit also includes a first container that contains an inorganic acid and an organic extraction solvent. The kit additionally includes a second sampling means that is a syringe configured to collect a predetermined amount of an organic solvent extract. The kit also includes a second container that comprises an organic base and an indicator. Using the kit, one would collect a predetermined amount of a coolant sample, and add the sample to a mixture of the inorganic acid and the organic extraction solvent. After mixing, the second syringe would be used to remove a portion of the organic solvent extract (organic layer) and the portion would be added to the organic base and indicator and mixed. The color of the indicator in the organic base would be observed and the color of the mixture would indicate whether the amount of the organic acid in the coolant was at or above an acceptable level or was below an acceptable level.

A second exemplary kit of the invention includes a first sampling means that is a syringe configured to obtain and dispense a predetermined amount of coolant sample. The kit also includes a first container that includes an inorganic acid and an organic extraction solvent. The kit additionally includes a second sampling means that is a syringe configured to collect a predetermined amount of an organic solvent extract and dispense that predetermined amount into a second container that comprises an aqueous base and an indicator. Using the kit, one would collect a predetermined amount of a coolant sample and add the sample to a mixture of the inorganic acid and the organic extraction solvent. After mixing, the second syringe would be used to remove a predetermined portion of the organic solvent extract (organic layer) and the portion would be added to the aqueous base and indicator and mixed. The color of the indicator in the aqueous base would be observed and the color of the indicator would indicate whether the amount of the organic acid in the coolant was at or above an acceptable level or below an acceptable level.

A third exemplary kit of the invention includes a first sampling means that is a syringe configured to collect a predetermined amount of sample. The kit also includes a first container that comprises an inorganic acid and an organic extraction solvent. The kit additionally includes a second sampling means that is a syringe configured to contain a predetermined amount of an organic solvent extract and that includes gradations to indicate the amount of the organic solvent extract expelled at the endpoint of a titration and calibrated to indicate the acid content in the coolant sample. The kit also includes a second container that comprises a base and an indicator. Such a kit is exemplified in FIG. 2 herein. Using the kit, one would collect a predetermined amount of a coolant sample, and add the sample to a mixture of the inorganic acid and the organic extraction solvent and mix. After mixing, the second syringe would be used to remove a predetermined portion of the organic solvent extract (organic layer) and the portion would be added in a controlled manner (e.g., drop wise) to the organic base and indicator that are in the second container. The indicator color would be observed during the addition and when the color change indicated that a predetermined titration endpoint was reached, the amount of the portion remaining in the second syringe could be determined by reading the gradations on the syringe, which provide a measure of the amount of the organic acid in the coolant.

A fourth exemplary kit of the invention also includes a titration means that includes an aqueous base and gradations calibrated to indicate the acid content of the coolant sample. The kit includes a first sampling means that is a syringe configured to obtain and dispense a predetermined amount of coolant sample. The kit also includes a first container that comprises an inorganic acid and an organic extraction solvent. The kit additionally includes a second sampling means that is a syringe configured to collect a predetermined amount of an organic solvent extract. The kit also includes a second container that comprises an indicator. Using the kit, one would collect a predetermined amount of a coolant sample, and add the sample to a mixture of the inorganic acid and the organic extraction solvent and mix. After mixing, the second syringe would be used to remove a predetermined portion of the organic solvent extract (organic layer) and the portion would be added to the indicator in the second container. The titration means would then be used to add in a controlled manner (e.g., drop wise), an amount of the aqueous base to the second container sufficient to have indicator color change indicate that a predetermined titration endpoint was reached. At that point of the titration, the amount of the aqueous base remaining in the titration means could be determined by reading the gradations on the titration means, which would provide a measure of the organic acid content in the coolant.

In some aspects of the invention, a kit may include one, two, or more containers that are vials and a kit may also include one, two, or more syringes. Vials useful in kits or methods of the invention may be made of any suitable material, including, but not limited to glass, flexible plastic, rigid plastic, solvent-resistant plastic, etc. Exemplary types of plastic vials include polypropylene vials, polystyrene vials, polymethylpentane vials, etc. A vial useful in methods and/or kits of the invention may be transparent, opaque, or translucent and may be used with or without a closure or lid. A vial used in a method and/or kit of the invention may be a screw-top vial, a crimp-top vial, a snap-top vial, or a vial that can be closed with a stopper or any other suitable closure means. Caps for vials used in methods and/or kits of the invention may be the same color or may differ in color. In some embodiments methods and/or kits of the invention, different cap colors may be used to code for vial contents. For example, a vial capped with one color cap and a vial with another color cap may be included in a kit, with the contents of the vials identified for the user by the cap color of each.

Syringes useful in a kit and/or method of the invention may be dimensioned and configured to obtain and/or expel a liquid in a controlled stream. A syringe that is useful in a method and/or kits of the invention may include graduations indicating volume. In some embodiments, the gradations may be gradations that can indicate the amount of a liquid that is expelled from, or drawn into the syringe. A syringe useful in a kit and/or method of the invention may include graduations on the syringe that include a scale of total organic acid content. A syringe useful in a method and/or kit of the invention may include gradations with a scale that is read out directly as a percent of full strength coolant or as a percent of full strength organic acid content of the coolant. In some aspects of the invention, a syringe useful in methods and kits may have no gradations or indications. In certain embodiments, a syringe may have a "stop" in the barrel (also referred to herein as the "cylinder") that limits the travel of the plunger in the barrel and thus, permits a predetermined volume to be picked up by the syringe. As used herein, a "stop" may be a ridge or other protuberance in the syringe barrel that prevents the plunger from being drawn past a set level, thus permitting the syringe to pull up a predetermined volume of liquid. Such a syringe may or may not comprise gradations or other volume indications.

Various embodiments of kits of the invention are contemplated. For example, in one aspect of the invention, a test kit includes a sampling syringe having a cylinder portion (also referred to herein as a barrel portion), a spout portion and a plunger. The plunger and cylinder portion may be dimensioned and configured so that a coolant sample drawn by the full travel of the plunger within the cylinder portion provides a precisely measured sample of known volume, e.g., 0.37 ml. Once the sampling syringe is filled with a coolant sample, suction sufficient to hold the coolant sample in place within the syringe can be maintained simply by leaving the plunger undisturbed in place. The kit also may include a resilient reaction container of generally test tube shape into which the coolant sample taken is deposited. An inorganic acid may be added to the sample in the resilient reaction container and an organic extraction solvent is then added and the resulting combination is mixed and allowed to separate, resulting in at least an organic layer that contains the protonated organic acid.

A second reaction container that contains a reactant species (e.g., an aqueous or organic reactant species) in a first frangible ampule and an indicator (e.g., phenol red) in a second frangible ampule may be part of a kit of the invention. The reactant species content of a first ampule may provide a basic species to react with the protonated organic acid of the organic layer added to the second reaction container from the first resilient reaction container. Both ampules in the second reaction container may be supported by an ampule holder that comprises a stiff but flexible split tube within which the ampules, which are of a diameter somewhat greater than the inside diameter of the split tube, are retained by the gripping pressure of the split tube. An ampule holder may be supported by a leg portion thereof that is seated at the bottom end of the reaction container. A reaction container of the invention may be sufficiently resilient so that the user may crush the frangible ampules to release the ampules contents by squeezing the outside of the reaction container. The reaction container can be made of any suitable resilient material that is sufficiently transparent to permit visual observation of the contents of the reaction container, to permit the user to observe mixing and separation of the reactants, etc., as described below. In some embodiments, screw threads may be formed adjacent to and extending from the mouth of a reaction container so as to enable the container to threadably receive a screw-on cap. The cap, which serves to close the container, is removable and replaceable on the container and may be fitted with a valve spout that has a spout conduit extending through, and has a cap conduit formed therein. A valve spout may be pivotably mounted within the cap so it is pivotable between a closed position and an open position. In the closed position the spout conduit is out of alignment with the cap conduit and seated against an interior wall of the cap whereby the spout conduit is sealed against flow therethrough. In the closed position, a valve spout may be flush with the flat top of the cap. In the open position, the valve spout may be disposed at right angles to the top of the cap and the spout conduit is in alignment with the cap conduit that extends through hemispherical the base portion of the cap to allow fluid flow from the interior of the container through the cap.

In use, a measured sample of the coolant to be tested may be taken, for example by drawing a quantity of coolant from an engine radiator, thoroughly mixing the sample and allowing cooling to ambient temperature if necessary. A sampling syringe may then be inserted into the thoroughly mixed coolant sample and the syringe plunger can be drawn fully back to fill the sampling syringe, taking care that no air bubbles are formed within the syringe. Alternatively, the coolant sample quantity may be taken by weighing the coolant sample. However, a volumetric sampling technique is simpler to carry out, especially in a field test kit designed for use by relatively untrained persons. If there are air bubbles, the sample is expelled and a fresh sample taken to completely fill the syringe so that a measured quantity of coolant sample is obtained. The exterior of the syringe tip inserted into the coolant can be wiped clean to remove therefrom excess coolant that might otherwise get into a first container and thereby increase the size of the sample introduced into the first container beyond the premeasured quantity contained within the barrel (cylinder portion) of the syringe. The user can remove the cap from the first reaction container and deposit the sample coolant from the sampling syringe into the first reaction container by depressing the plunger to expel the entire measured coolant sample from the syringe into the first reaction container.

In some embodiments of the invention, the resident species (organic acid) in the sample coolant is first protonated and then is mixed with an organic extraction solvent (e.g. an organic solvent) in which the protonated resident species is soluble. The solvent dissolves the coolant sample to produce at least an organic layer (also referred to herein as an organic solvent extract and solvent phase coolant sample) that includes the protonated organic acid species.

The use of frangible ampules in some embodiments permits the order of mixing of the various components to be selected, which provides for flexibility in selecting a test strategy. For example, a portion of the organic layer from the first container can be added to a second container, and then the user can squeeze the second container to crush the first frangible ampule and mix the organic layer portion with the reactant species, then the user can squeeze the container to crush the second ampule, thus releasing the indicator into the organic layer/reactant mix. Alternatively, to mix the indicator and the reactant species in the container, the user may squeeze the container to crush the first frangible ampule, thus releasing the premeasured quantity of the reactant species into the container. The user then squeezes the container to crush the second frangible ampule, thus releasing the premeasured quantity of the indicator and shakes the container to thoroughly mix the contents. A portion of the organic layer from the first container is then added to a second container and the contents mixed. Some or all of the basic reactant species reacts with and is consumed by the protonated organic acid species.

After the protonated organic species has been contacted with the reactant species and the pH indicator, either by mixing or by titration, the user may readily observe the condition of the indicator to determine the pH level of the mixture and thus determine the organic acid content present in the coolant sample tested.

In some embodiments, it is desired to titrate an organic layer and indicator mixture with the reactant species to quantitatively determine the organic acid content of a coolant. For this purpose, the test kit may include a titration syringe that contains a titration liquid, in this case a solution of a basic reactant species, such as a solution of a base, e.g., NaOH or KOH. Using a titration syringe, titration liquid is added to a mixture of a portion of the organic layer and a pH indicator, until the pH indicator reaches its endpoint. The quantity of the basic solution thus delivered to the organic layer/indicator mixture is indicative of the organic acid content of the coolant sample tested.

In some embodiments, a kit may include a resilient titration container to which can be added a measured quantity of the organic layer from a first container. A titration container may contain a pH indicator in a third frangible ampule, which is supported by an ampule holder similar to the ampule holder in the first reaction container. The indicator may comprise a conventional phenyl red solution or may be any other suitable indicator. As a non-limiting example, an indicator may comprise 200 microliters of a pH indicator in ethanol, which is released into the organic layer portion by crushing the third ampule by squeezing the resilient titration container from the outside. Like the reaction container, the titration container may be of generally test tube shape and is made of material that is sufficiently resilient to recover its shape after being squeezed sufficiently to crush the frangible ampule contained therein, and sufficiently transparent to permit the user to observe conditions and colors within the containers. Containers used in methods and kits of the invention may be made of any suitable resilient material, e.g., polyethylene, polystyrene, etc. and may be identical to eliminate the need to stock and provide two different types of container. In some methods and kits of the invention, a volume-indicating mark (described below) may be on one or more of the containers. The caps used on, respectively, different containers may be differently colored to facilitate following instructions, which may form part of the test kit.

Once the pH indicator has been added to the fixed amount of the organic layer portion in a titration container, the user may readily observe the condition of the indicator to determine the pH level of the extractant and thus determine the quantity of organic acid species present in the coolant sample tested. This observation is advantageously accomplished by titration, so that the organic acid content of the sample coolant can be quantitatively determined. For this purpose, the test kit includes a titration syringe, a non-limiting example which is provided as a titration syringe that contains a titration liquid, in this case a solution of a reactant species, such as a basic reactant species, e.g., NaOH or KOH. The titration liquid is added to the mixture of the organic layer portion/pH indicator in a container until the pH indicator reaches its endpoint. The quantity of reactant solution thus delivered to the reach the endpoint is indicative of the organic acid content of the coolant sample tested.

In an illustrated embodiment, a titration syringe contains a solution of sodium hydroxide, as the titration liquid. It will be understood that a titration syringe is a non-limiting example of a syringe or tool/utensil useful in methods and kits of the invention, and that alternative syringe configurations or other suitable tools/utensils can be used in methods and kits of the invention. A titration syringe useful in kits and methods of the invention may be made from a molded plastic material and generally may comprise a conventional cylindrical body (e.g. barrel) that has a discharge spout that in some embodiments of the invention can be closed by a break-away closure tip that closes off the discharge spout. A plunger head can be slidably received within the body (e.g., barrel) at the end of the body furthest removed from the discharge spout. A plunger head may be snugly received within the syringe barrel and may include sealing collars that can provide a liquid-tight seal within the barrel so that a titration liquid is sealed within the body, between the plunger head and closure tip. The plunger of a titration syringe is conveniently provided separately, that is, not mounted in the plunger head. This shortens the length of a titration syringe for packaging and shipment.

In some embodiments of the invention, a threaded syringe cap may be slidably mounted on the body of a titration syringe. Threads of the cap are dimensioned and configured to be threadably received on the threads of the titration container, so that the syringe may be mounted upon a container with the discharge spout of the syringe positioned within the titration container. The diameter of an ampule holder may be small enough relative to the inside diameter of a titration container that the ampule holder would not impede the insertion of the body (e.g. barrel) of the syringe within the titration container.

A plunger rod may be sized to be received within the barrel of a titration syringe and may have an insertion tip that is dimensioned and configured to be snap-fitted within a cavity of the plunger head. A titration syringe useful in some embodiments of the invention, may have applied graduations that are scaled and numbered to directly correspond to the organic acid content of a tested coolant sample as indicated by the volume of titration liquid, e.g. a basic solution (NaOH) required to titrate the organic layer portion to the indicator endpoint. In the case of the specific reagents exemplified in the foregoing description, the endpoint is seen as a change in color from red to orange/yellow. Therefore, when the user can employ a titration syringe to titrate the organic layer portion to the endpoint of the pH indicator, the number of the graduation at which the plunger comes to rest gives the organic acid content number of the coolant sample. This obviates the need for the user to perform any calculations to determine the organic acid content number of the sample. Alternatively, the kit may comprise a color chart giving the pH and/or the organic acid content number of the sample when the pH indicator attains a particular color shade. This latter technique may be used as an alternative to, on in conjunction with, the use of graduations on the titration syringe. Use of a titration liquid as opposed to premeasured quantities of titer enables use of infinitely small increments of titer and a correspondingly more accurate test.

When the user is ready to carry out a titration step, the container is shaken to thoroughly mix the pH indicator released from the ampule and the organic layer portion. The user then places the insertion tip of the plunger rod into a cavity of the plunger head and snaps the insertion tip into place. Then, the user removes the cap from the container, breaks off the closure tip of the titration syringe, inserts the titration spout into the titration container, and screws the cap into place on the threads of the titration container. The plunger head, as noted above, may be positioned within and may seal the top of the body of the syringe. The opening resulting from the breaking tip is small enough so that there is no leakage of titration liquid before the plunger is operated. With this arrangement, in which the cap seals the titration container, the titration may be performed without the risk of spilling any titration solution or organic layer portion even while gently shaking the titration container as titration liquid is added, in order to completely mix the titration liquid with the contents of the titration container. The user may then perform the titration by slowly depressing the plunger of the titration syringe to expel the basic reactant species titration solution from the syringe into a container, while constantly gently shaking the container. Occurrence of the endpoint is indicated by a color change: in the specific case exemplified, by a color change from magenta to yellow. The resistance offered by the tight fit of the plunger head within the body of the titration syringe holds the plunger in place at the point where the user stops pushing it to expel the titration solution. This permits the user to easily read the organic acid content value directly from the graduations printed on barrel by noting the graduation at the bottom or forward end of plunger head. For example, if the plunger is advanced to a position somewhat more than half of its total travel distance when the titration endpoint occurred, the organic acid content would be read by the user at the point on the graduations marked by the bottom end of the plunger head.

The kits and kit components are non-limiting examples and are not intended to limit the types of containers, sampling means, titration means, or reagents that can be included in a kit of the invention.

EXAMPLES

Example 1

Assay Development for Determining Levels of Organic Acid in Extended Life Coolants (ELCs)

ELCs (Extended Life Coolant) are based on Organic Acid Technology (OAT) major acids used are 2-ethylhexanoic acid (EHA), benzoic acid, neodecanoic acid, and sebacic acid. Other ingredients in ELC coolants may include KOH, ethylene or propylene glycols and water (50%). Neodecanoic acid is a mixture of carboxylic acids with the common structural formula $C10H20O2$, a molecular weight of 172.26 g/mol, and the CAS No. 26896-20-8. Components of the mixture are acids with the common property of a "trialkyl acetic acid" having three alkyl groups at carbon two, including: 2,2,3,5-Tetramethylhexanoic acid; 2,4-Dimethyl-2-isopropylpentanoic acid; 2,5-Dimethyl-2-ethylhexanoic acid; 2,2-Dimethyloctanoic acid; 2,2-Diethylhexanoic acid.

EHA is not soluble in water unless it is in the ionic form (typically a strong base is added to the coolant to keep the EHA in solution), so if enough acid is added to an aqueous coolant, the EHA comes out of solution. The EHA can then be captured in an organic extraction solvent, separated from the coolant, and the amount of organic acid in the coolant can subsequently be determined using various methods. For example, the amount of protonated organic acid can be determined using a Total Acid Number (TAN) test typically used to analyze lubricants. TAN test kit (Dexsil, Hamden, Conn.) may be used. Methods of running TAN tests are set forth in U.S. Pat. Nos. 5,366,898, and 5,800,782, which are incorporated herein by reference in their entirety. Other methods can also be used to determine organic acid content in an ELC once the acid in the ELC has been protonated using an inorganic acid and the protonated organic acid solvated in an organic extraction solvent. Non-limiting examples of such methods are ASTM methods D-664 and D-974.

Test 1

The amount of EHA in an organic solvent was determined. In protonated form EHA dissolved readily in iso-octane and should dissolve in most other non-polar solvents. Iso-octane is a solvent that does not mix with or entrain any water.

Test 2

Figure 3:
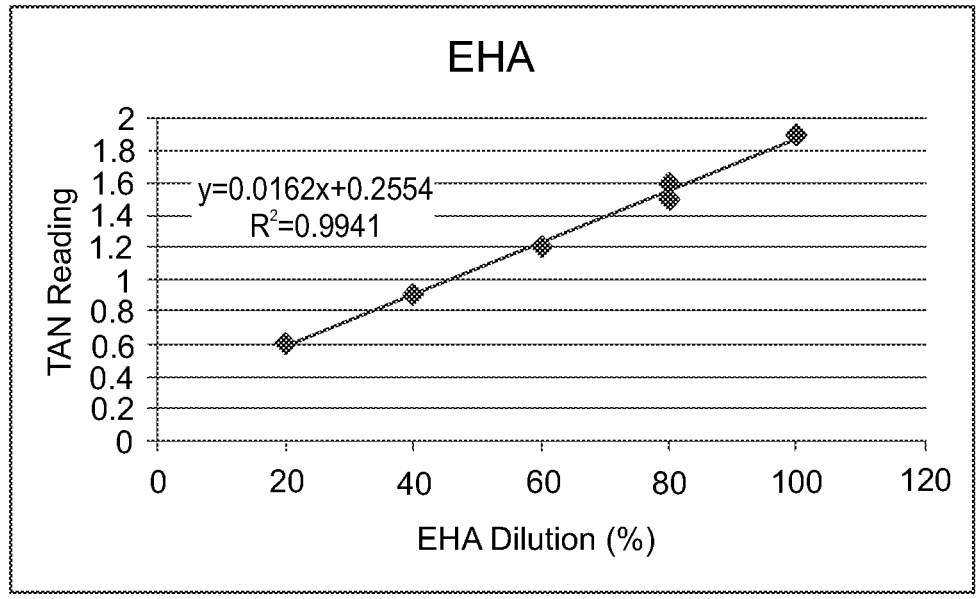
FIG. 3 shows a graph of results of the titration of 2-ethyl-hexanoic acid (EHA) determined using a total acid number test.

The titration of EHA was determined using a Total Acid Number (TAN) test kit. Standards of EHA in iso-octane were prepared in a range of levels expected to be in coolant. Table 1 and FIG. 3 show results of the Total Acid Number (TAN) test and demonstrated the feasibility of titrating EHA using this method. The samples were reacted with a fixed amount of NaOH and extracted into an aqueous phase where excess NaOH was titrated to determine the amount of EHA that was reacted.

TABLE 1

| EHA % | Acid Number |
|---|---|
| 100 | 1.9 |
| 80 | 1.6 |
| 80 | 1.5 |
| 60 | 1.2 |
| 40 | 0.9 |
| 20 | 0.6 |

Test 3

Figure 4:
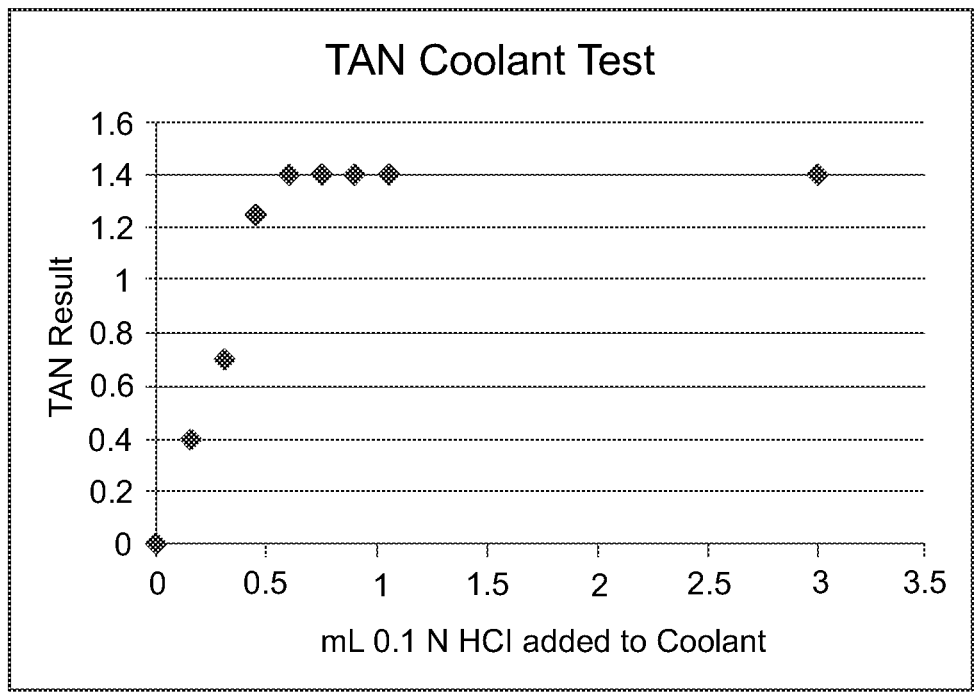
FIG. 4 shows a graph of results of tests to determine the amount of acid to add to coolant to precipitate all of the EHA present.

Tests were run to determine the amount of acid to add to a coolant sample to fully protonate all of the EHA present. For the tests, a sample of full-strength (100% EHA) coolant was obtained using a sampling syringe (in this test a 0.4 mL syringe was used, but any suitable syringe could be used). 1 mL of deionized (DI) water was added. Varying amounts of 0.1N HCl were added and the following tests were run:

2.24 mL of organic extraction solvent (iso-octane) were added. A 0.8 mL sample was taken from the organic layer and an acid number test, as in Test 2, was run on the sample. The acid number could be scaled to read out in % EHA. Results are shown in Table 2, and FIG. 4.

TABLE 2

Test results for Organic Layer Extraction test.
.4 ml coolant, 1 ml DI water, 0.1N HCl, 2.24 mL of isooctane

| N | mL of 0.1N HCl | pH | Acid Number |
|---|---|---|---|
| 0 | 0 | 6.5 | 0 |
| 1 | 0.15 | 6 | 0.4 |
| 2 | 0.3 | 5 | 0.7 |
| 3 | 0.45 | 5 | 1.25 |
| 4 | 0.6 | 4.5 | 1.4 |
| 5 | 0.75 | 4 | 1.4 |
| 6 | 0.9 | 4 | 1.4 |
| 7 | 1.05 | 4 | 1.4 |
| 8 | 1.2 | 4 | |
| 9 | 1.35 | 4 | |
| 3 ml HCl | 3 | 3.5 | 1.4 |

Test 4

Figure 5:
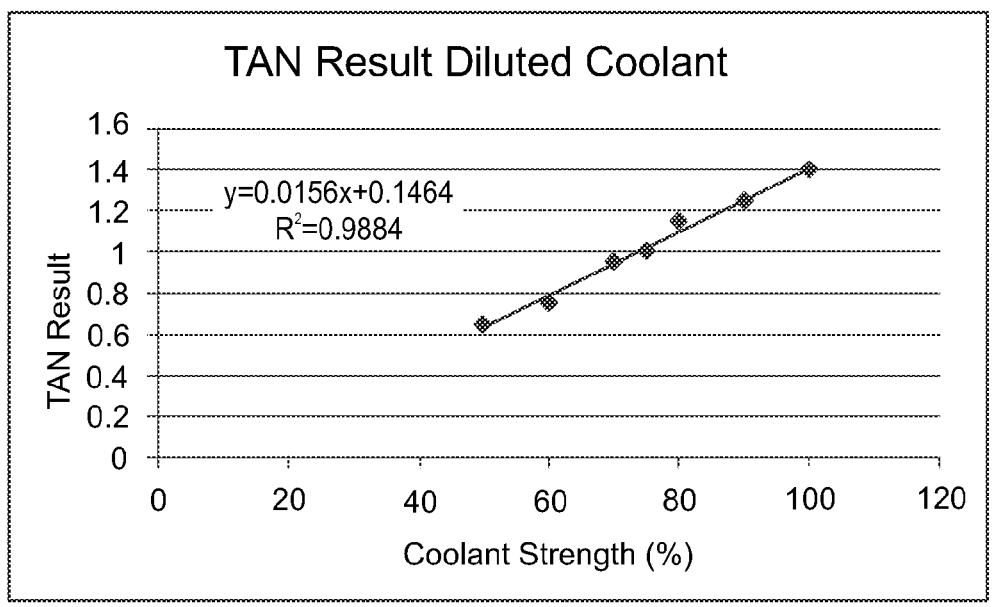
FIG. 5 shows a graph of results of linearity testing on diluted coolant.

Test 3, as described above, was run using optimal amount of acid on diluted coolant to establish linearity. Results are shown in Table 3 and FIG. 5.

TABLE 3

Linearity testing on diluted coolant.

| Coolant strength (%) | Total Acid Number |
|---|---|
| 100 | 1.4 |
| 90 | 1.25 |
| 80 | 1.15 |
| 75 | 1 |
| 70 | 0.95 |
| 60 | 0.75 |
| 50 | 0.65 |

Other non-OAT silicate/phosphate based coolants were tested and resulted in 0 or negative Total Acid Number (TAN), Prestone® Dual Action Formula, Auto Pride® Antifreeze & Coolant, AutoZone® Conventional Green and ProLine® Antifreeze & Coolant.

Other ELCs tested were: Prestone® Universal Coolant, TAN result was 1.55; Peak® LongLife® read 1.3; Prestone® Dex-Cool® read 1.65 and AutoZone® DEXCoo10 and Universal both read 1.4.

Test 5

A simplified version of the test was performed and included running the first part of the test up to the adding of the iso-octane and taking the 0.8 mL sample of the organic layer. 1 mL of deionized (DI) water was added to the 0.8 mL sample and then a methyl red indicator was added. The mixture was titrated to yellow color using a calibrated syringe containing a base such as that available in a TBN test kit (Dexsil, Hamden, Conn.). The value was read off the syringe. The reading was 16.5, which was scaled for a back titration. Methods of performing a TBN test are set forth in U.S. Pat. Nos. 5,366,898, and 5,800,782, which are incorporated herein by reference in their entirety. For some applications, the indicia on the container or syringe can be marked to show the organic acid level directly.

Test 6

In another test, a 0.8 mL sample of organic layer was obtained and a fixed amount of NaOH was added. Methyl red was also included as an indicator. If the mixture stayed red, the percentage of organic acid was below 75% and if it turned yellow, the percentage was above 75%.

Tests were then run to determine the level of NaOH necessary to give a "Fail" result at 75% coolant. For the procedure, the first part of test was run as above. A 0.8 mL of sample of the organic layer was added to a polyethylene tube containing: 1 mL deionized water and a methyl red indicator ampule. 1.2 mL of 0.1N NaOH was added. The test was run with a series of coolants using methyl red indicator. Results provided orange indicator color at 100% and 80% ("Pass" levels) and yellow indicator color at 75%, 70% and 50% ("Fail" levels). The same test was run using the indicator p-Naphtholbenzein and the series was run. For this test, results provided orange indicator color at 100% and 80% ("Pass" levels) and blue indicator color at 75%, 70% and 50% ("Fail" levels). The procedure was the same as with the methyl red except 0.138 mL of 0.1N NaOH was used.

Test 7

In this test the methods and formulations of Test 6 were used, except instead of adding the full 0.8 mL of the organic layer, a graduated syringe was used to add the sample drop wise until the endpoint color was obtained. After the endpoint was reached, the scale was read to determine the volume of sample required to reach the color change. Kits can include syringes on which the scale is read out directly as a percent of full strength.

Figure 6:
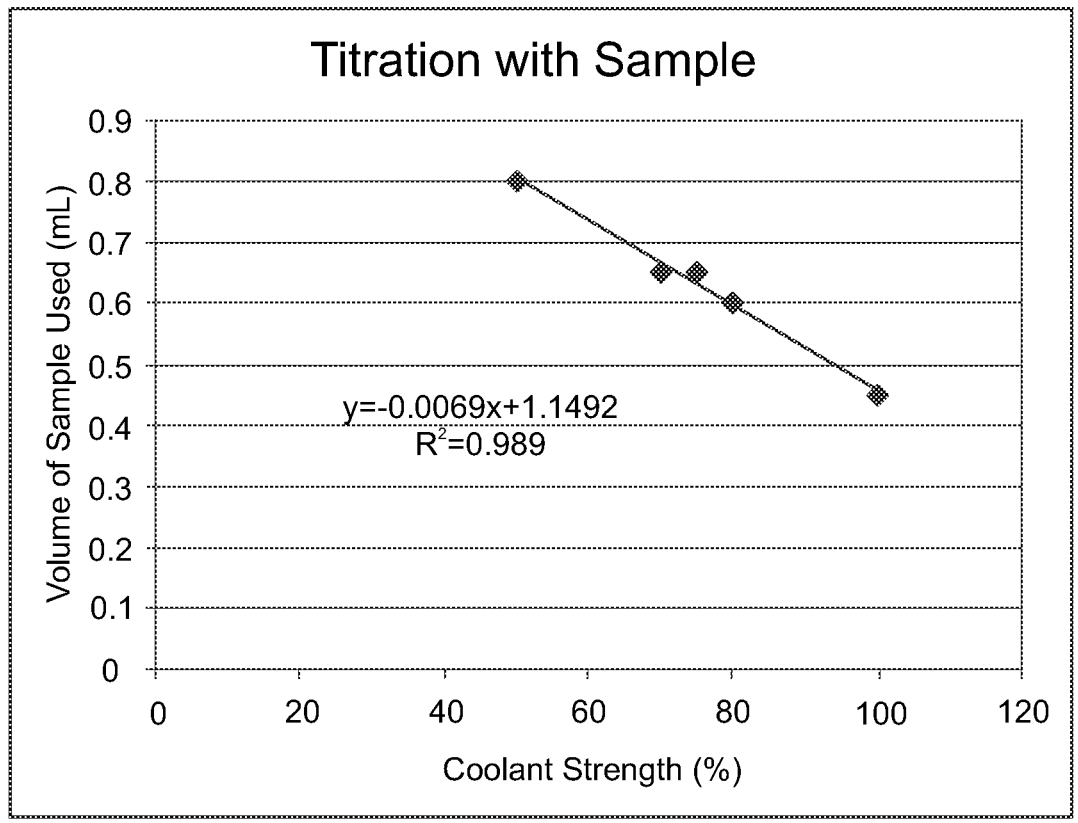
FIG. 6 provides a graph showing the results of a titration using different percentages of coolant. The coolant strength is the percentage of organic acid in the coolant and the volume of sample used (ml) is the amount of sample required to reach the color change. The graph illustrates that the higher the coolant strength, the lower the volume of sample needed to titrate to the color-change endpoint.

In this experiment, the final aqueous solution was 0.966 mL of 0.01N NaOH with 0.4 mL of pH indicator (p-Naphtholbenzein in EtOH). Results of the titration are shown in FIG. 6 and Table 4. The "Sample %" is the OAT strength of the coolant, with 100% being equivalent to brand new, unused ELC. The term "ml left" is the amount of the organic layer left in the syringe, and the term "ml sample" is the amount of the organic layer required for the color change. With a higher percentage of organic acid in the coolant, less of the organic layer sample needed to be added from the syringe to reach the color change endpoint.

TABLE 4

Data showing the volume of sample added to reach the indicator color change.

| Sample % | ml left | ml sample |
|---|---|---|
| 50 | 0 | 0.8 |
| 70 | 0.15 | 0.65 |
| 75 | 0.15 | 0.65 |
| 80 | 0.2 | 0.6 |
| 100 | 0.35 | 0.45 |

Test 8

Organic Acid Recovery Using Different Solvents

The following data was obtained by testing different organic acid technologies (OATS). The results demonstrate how the solvent can be tailored to exclude different OATs from detection.

To determine recoveries of different OATs in various organic solvents, synthetic "coolants" were made up using the different organic acids. The coolants were made up at known concentrations in 50% ethylene glycol with NaOH to neutralize the acid and provide roughly the same amount of reserve alkalinity as in a normal coolant.

OATs tested included: EHA, Benzoic, Decanoic, Sebacic

Solvents Tested: Isooctane, PA7, Shellsol D60, Butyl Diglyme

Each OAT coolant was tested twice using the following procedure:

1) 0.4 mL of coolant, 1 mL of $0.075NH_2SO_4$ and 2.24 mL solvent were combined and then shaken to mix.
2) 1 mL of the organic layer was taken from the mixture and added to 2 mL thymol blue indicator.
3) The mixture and indicator were titrated with 0.05N NaOH.

Figure 7A:
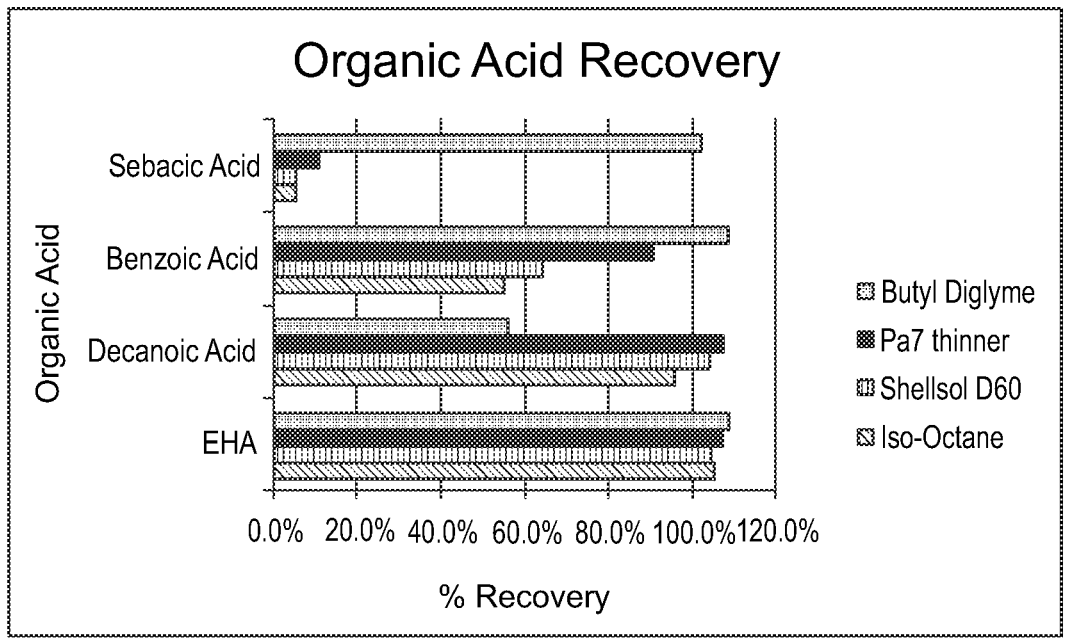
FIG. 7 provides graphs indicating recoveries of different OATs in various organic solvents.
Figure 7B:
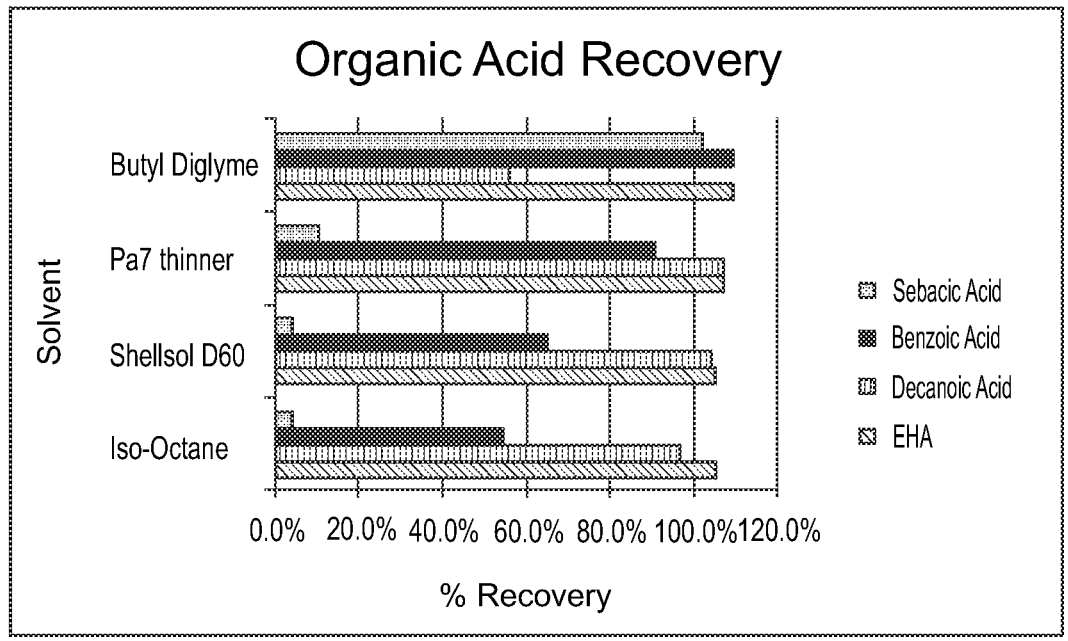
Figure 8A:
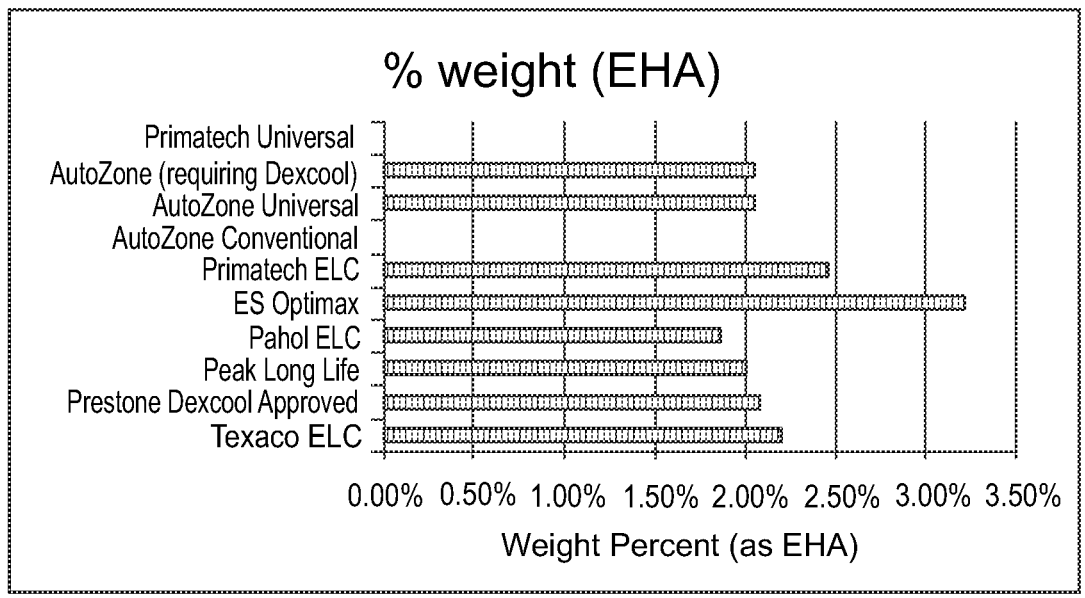
FIG. 8 provides graphs of weight percent and normality of various commercial coolants.
Figure 8B:
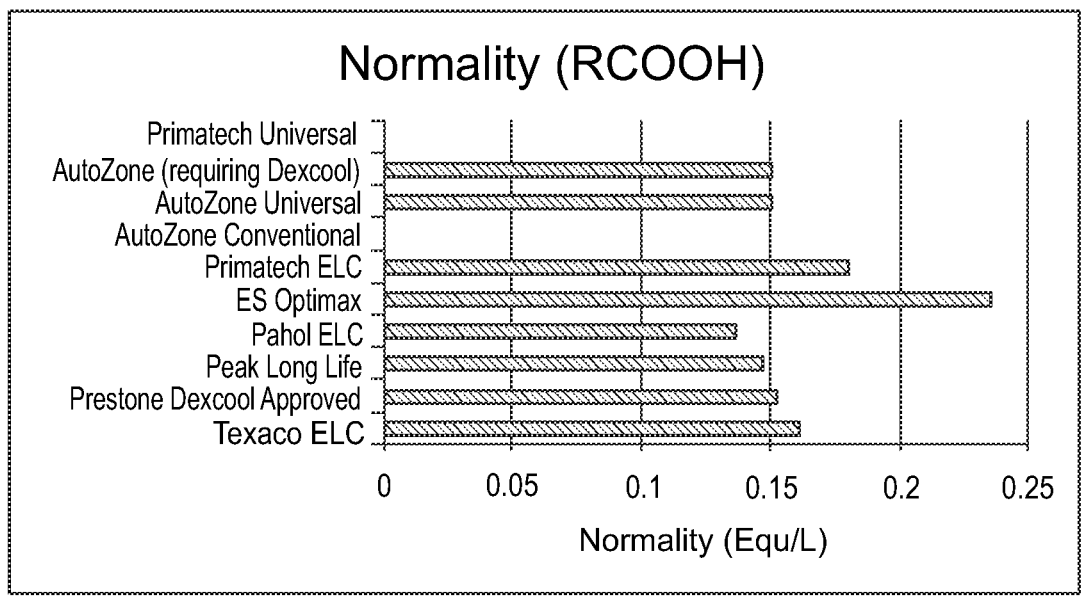
Figure 9:
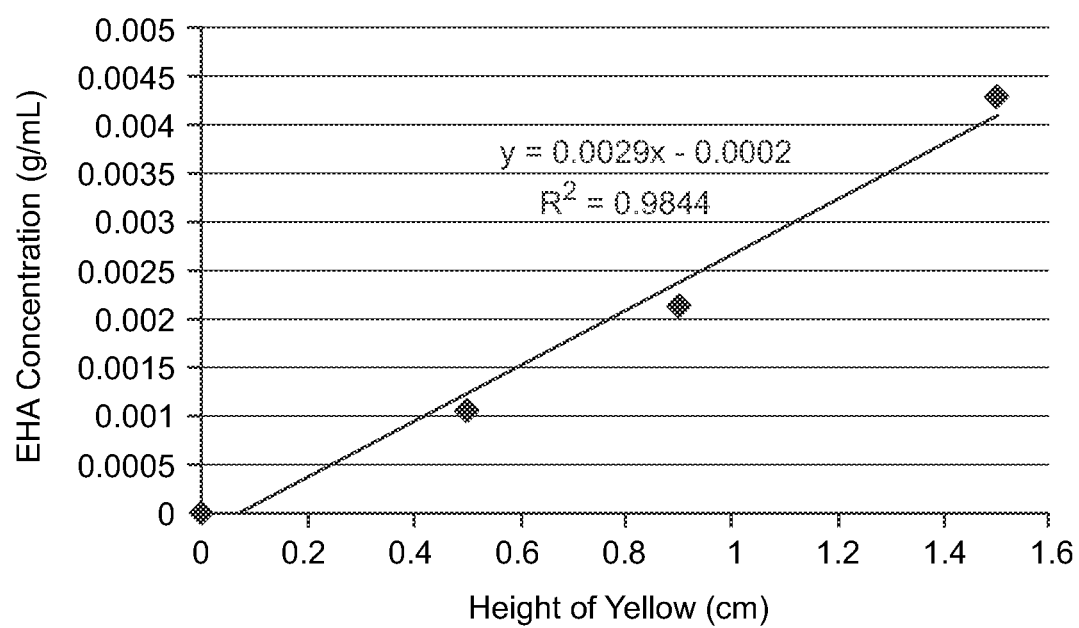
FIG. 9 provides graphical results showing the height of color change in a solid phase pH indicator as a function of EHA concentration in a solvent system.

Average recovery of the results of the two tests are provided in Table 5 and are shown in FIG. 7. The results indicated that butyl diglyme was the only solvent that worked with sebacic acid. The recovery for decanoic acid in butyl diglyml was, however, low. Combining PA7 and butyl diglyme in a 50/50 mixture did not improve the recovery of decanoic acid, but did not decrease the recovery of the other acids. Using a 25/75 butyl diglyme/PA7 solvent improved the recovery of decanoic acid to 80% and lowered the recovery of sebacic acid to near 70%.

TABLE 5

Average percent recovery of OATs tested with solvents.

| | EHA | Decanoic Acid | Benzoic Acid | Sebacic Acid |
|---|---|---|---|---|
| Iso-Octane | 105.2% | 96.2% | 55.1% | 5.0% |
| Shellsol D60 | 104.8% | 104.3% | 64.5% | 5.0% |
| PA7 thinner | 107.4% | 107.4% | 90.9% | 11.0% |
| Butyl Diglyme | 108.8% | 56.0% | 108.7% | 102.3% |

Example 2

Assessment of Parameters in Methods to Determine Levels of Organic Acid in Extended Life Coolants (ELCs)

Tests were performed to assess solvents, indicators, and inorganic acids, etc. Tests using various commercially available coolants were performed using various indicators and under various parameters. For these experiments, the hypothetical condemning limit of 75% of full strength was used as the color-change target endpoint.

Solvent Tests

Tests were performed to determine the suitability of different organic extraction solvents. Using the fixed endpoint test from Test 6 of Example 1, different solvents were tested. Each test was run twice.

Steps in the tests were as follows:

Step 1) 2.24 ml solvent was added to 0.6 ml 0.1N HCl and 0.4 ml coolant sample and the mixture was shaken for 30 seconds and allowed to separate.

Step 2) 0.8 mL of the resulting organic layer removed and added to 2 mL 0.008% Cresol Red in 0.006 N NaOH.

Test results are provided in Table 6, which shows indicator color results for various organic extraction solvents and solvent concentrations that were tested. The color change was shifted slightly so for a final test the amount of base in the final vial is adjusted to give the best color change. For example, if recovery of the protonated acid improved, the acid level in the final solution was higher, causing a shift toward the indicator color at the 100% end of the spectrum. To keep the color at the basic end of the spectrum (fail end), more base should be added.

TABLE 6

Solvent test results.

| Coolant and Strength | Trial 1 | Trial 2 |
|---|---|---|
| Odorless mineral spirits | | |
| 80% coolant- | orangey yellow | yellow |
| 75% coolant- | light orange | orangey yellow |
| 70% coolant- | purple | red |
| HISOL #10 | | |
| 80% coolant- | yellow | yellow |
| 75% coolant- | yellow | orangey yellow |
| 70% coolant- | orangey yellow | orange |
| PA7 Thinner (HISOL 150) | | |
| 80% coolant- | orangey yellow | yellow |
| 75% coolant- | orangey yellow | yellow |
| 70% coolant- | orange | orange |

Indicator Selection

Various indicators were tested to first see if they would work on the fixed endpoint test. (Procedure as described above). The criteria were sharp endpoint, clear color difference and, whether the indicator could be made up in the base solution of the last vial and have reasonable shelf life. Tests were run using solvents PA7 and isooctane.

Tests were run using the following indicators:
p-Naphtholbenzein—did not last with base.
Methyl red—red to yellow did not last with base. Difficult to get a good range.
Bromocresol purple-yellow to purple. Did not show significant change. Colors were very close.
Bromophenol blue-did not change with 0.8 ml sample. pH range was too low.
Congo red-pH change was too low. Difficult to change solution color with EHA.
Chlorophenol red-did not dissolve well.
Bromocresol green-green to blue. Visible change but not as clear as some others.
Bromophenol red-yellow to purple. Worked.
Phenol red-yellow to pink. Worked well. (aging*)
Cresol Red-yellow to purple. Worked well. (aging*)
Thymol blue-yellow to blue. Worked. (aging*)
Note: * "aging" was performed by letting the premeasured reagents stand in a dark drawer and retesting periodically to see how they performed after time.

The three indicators that worked best were phenol red, cresol red, and thymol blue. Other indicators that did not work as well can be used in other circumstances and conditions. Indicator solutions of phenol red, cresol red, and thymol blue were prepared having the correct amount of base already in them, based on a 1 mL total volume of indicator solution with 0.4 ml coolant sample. Vials were prepared to test shelf life and all three were still active after five months.

Different Types of Acid

Different inorganic acids (for protonating the organic acids) were tested for their use in the assays. The acids were initially tested using iso-octane as the non-polar phase, because iso-octane had been shown to work and any problems could be attributed to the acid. Sulfuric acid, hydrochloric acid, and nitric acid were tested.

Several acids were tested with PA7 Thinner and three indicators. Results are shown in Table 7.

TABLE 7

Acid test results with PA7 Thinner and three indicators.

| | Thymol blue | Phenol red | Cresol red |
|---|---|---|---|
| Sulfuric Acid | | | |
| 100% coolant | Yellow | Orangey yellow | Yellow |
| 80% coolant | Yellow | light orange | golden yellow |
| 75% coolant | Yellow | red-orange | dark orange |
| 70% coolant | Grayish blue | red | purple |
| 50% coolant | Bright Blue | pink | purple |
| Nitric Acid | | | |
| 100% coolant | Yellow | Orangey yellow | Yellow |
| 80% coolant | Yellow | orange | golden yellow |
| 75% coolant | Greenish Yellow | dark orange | dark orange |
| 70% coolant | Gray blue-Green | red | pink |
| 50% coolant | Bright Blue | pink | purple |
| HCl | | | |
| 100% coolant | Yellow | Orangey yellow | Yellow |
| 80% coolant | Yellow | orange | golden yellow |
| 75% coolant | Blue-gray | dark orange | red |
| 70% coolant | Gray-blue | red | purple |
| 50% coolant | Bright Blue | pink | purple |

Test of Method on Various Commercial Coolants

Different types of coolant were tested with PA7 thinner and sulfuric acid and all three indicators. (0.2 ml indicator, 0.8 ml water, 0.8 ml extraction from coolant) The indicators were adjusted because the coolants have different percentages of organic acid. The original indicator solution having only a small amount of base was used and then 0.1N NaOH was added until the 70% coolant failed in tests. Results are provided in Table 8 and in FIGS. 10-13 as indicated.

Table 8: Results of commercial coolant tests on full strength (100%), 80% and 70% ELC.

Autozone® Conventional Green:
All three coolant percentages failed with all three indicators when tested with this conventional coolant, which is not an organic acid technology (OAT) coolant.

Autozone® Universal
Thymol blue: 0.131 ml 0.1N NaOH was added.
100%-yellow, 80%-greenish-yellow, 70%-blue
Phenol Red: 0.17 ml 0.1N NaOH was added.
100%-light orange, 80%-dark orange, 70%-pink
Cresol Red: 0.124 ml 0.1N NaOH was added.
100%-yellow, 80%-light orange, 70%-purple Autozone® Dexcool®
Thymol Blue: 0.135 ml 0.1N NaOH was added.
100% yellow, 80% yellow, 70% blue
Phenol Red: 2× volume B51200A worked.
100% yellow, 80% orange, 70% red
Cresol Red: 0.13 ml 0.1N NaOH was added.
100% yellow, 80% yellow, 70% purple Peak® Long Life®
Thymol Blue: 2× volume B51200C worked.
100% yellow, 80% greenish yellow, 70% slate blue
Phenol Red: 2× volume B51200A worked.
100% yellow, 80% light orange, 70% pink
Cresol Red: 2× volume B51200B worked.
100% yellow, 80% light orange, 70% dark pink Prestone® Dexcool®
Thymol Blue: 2.0 ml 0.1 NaOH was added.
100% yellow, 80% yellow green, 70% blue-gray
Cresol Red: 1.8 Ml 0.1N NaOH was added.
100% yellow, 80% light orange, 70% pink Phenol Red: did not work due to poor color separation. All three turned orange and 80% and 70% were indistinguishable.

Example 3

Concentration of OATs in Commercially Available Full Strength Coolants

In this experiment 11 coolants were tested using the above procedure provided in Example 1, Test 8, and the 25/75 butyl diglyme/PA7 solvent system.

The results for the experiment are presented both as normality and as a weight percent using a nominal formula weight of EHA for conversion. The extraction step for ES Optimax and Primatech ELC remained cloudy indicating that they may have had a higher OAT concentration that was not fully protonated. These two samples were rerun using twice the amount of sulfuric acid in the extraction step and the results went up by a measurable amount. The higher result obtained with the greater amount of sulfuric acid is reported. Results are provided in Table 9 and FIGS. 14A and B.

TABLE 9

Normality and weight percent of OATs in various commercial coolants.

| Coolant | Normality (RCOOH) | % weight (EHA) |
|---|---|---|
| Texaco ® ELC | 0.1624 | 2.20% |
| Prestone ® Dexcool ® Approved | 0.154 | 2.08% |
| Peak ® Long Life ® | 0.1454 | 2.01% |
| PahNol ™ ELC | 0.1372 | 1.86% |
| ES Optimax ™ | 0.238 | 3.22% |
| Primatech ™ ELC | 0.182 | 2.46% |
| AutoZone ® Conventional | 0 | 0.00% |
| AutoZone ® Universal | 0.1512 | 2.05% |
| AutoZone ® (requiring Dexcool ®) | 0.1512 | 2.05% |
| Primatech ™ Universal | 0 | 0.00% |

Example 4

Methods and calculations of the invention are used to determine the amount or percentage of organic acid in an OAT coolant sample is as follows. A coolant sample is placed into a first container (e.g., Tube 1) along with a solvent such as iso-octane, mineral spirits, PA7 Thinner, butyl diglyme, or a mixture thereof; and an inorganic acid such as a mineral acid (e.g. HCl, H2SO4, HNO3, etc.). The mixture is shaken, allowed to separate, and an aliquot of the organic layer is removed and placed into a second container (e.g. Tube 2), where it combines with an indicator and is titrated with base, such as NaOH or KOH, (referred to herein as a reactant species), until the titration endpoint is reached. Calculations are carried out as follows to determine the concentration of organic acid in the coolant sample and to determine the percentage of organic acid in the coolant sample versus the percentage of organic acid in original 100% fresh coolant.

An amount of OAT coolant for testing is placed in Tube 1. An amount of solvent is added to the OAT coolant sample in Tube 1 and the contents is mixed thoroughly then allowed to separate. An amount of solvent is removed from the OAT-solvent mixture that has been allowed to separate in Tube 1, and is placed into Tube 2 where it is titrated using a base such as NaOH until the titration endpoint is reached. Reaching the endpoint is determined using an indicator.

For the calculations, X mL of coolant sample is placed into a first container (e.g., Tube 1) along with Y mL of a solvent and an inorganic acid. The mixture is shaken, allowed to separate, and an aliquot (Z mL) of the organic layer is then removed and placed into a second container (e.g. Tube 2), where it is titrated with n mL of a base of concentration C. An indicator is included in Tube 2, and the color change of the indicator is observed as a measure of the status of the titration endpoint.

Calculations can be done as follows to determine the concentration of organic acid in the tested coolant sample and to determine the percentage of organic acid in the coolant sample versus the percentage of organic acid in the original 100% fresh coolant.

The concentration of organic acid in a coolant is equal to:

$$\frac{nC(Y/Z)}{X}$$

In some embodiments, a correction factor may be employed to compensate for extraction inefficiencies and the like. The above calculation provides the concentration of organic acid in the coolant. To determine the percentage of organic acid in the coolant, the value from above is divided by the concentration of organic acid in full strength coolant and then multiplied by 100.

Example 5

To test the viability of a solid phase indicator, a series of experiments were completed using an EHA standard in an organic solvent. In one experiment a 0.14% solution of bromothymol blue in alcohol (ethanol) with 0.01N NaOH was spread on Whatman GF/F filter paper. After the alcohol dried, a drop of EHA (2-Ethyl Hexanoic Acid) standard (0.0043 g/mL in 25/75 v/v butyldiglyme/PA7) was placed on the treated filter paper. The treatment spot turned from blue to bright yellow and was easily discernible without the aid of instrumentation. As a control, a drop of the 25/75 solvent, without EHA, was added to another spot on the treated filter paper, and it did not turn yellow.

Example 6

In another test of a solid state indicator embodiment, strips of GF/F paper were prepared by dipping standard commercially available filter disks in a 0.28% BTB/0.01N NaOH alcohol solution and allowed to dry. The dry disks were then cut to thin strips about 5 cm long and heat laminated using 3 mil laminating pouches made of EVA. The laminated strips were then cut out so that 1 short edge of the filter paper was exposed and the entire strip was narrow enough to fit into a 25 mL scintillation vial. After lamination, the blue paper turned slightly green indicating an interaction with either the plastic laminate or the paper caused by the heat of lamination. The strips were placed into 4 different scintillation vials containing either the EHA standard from Example 5 or a 50% strength EHA standard or a 25% strength standard or EHA-free solvent (control). The results were: the strip in the full strength EHA standard turned completely yellow, the 50% standard turned yellow but retained a hint of green, the 25% strip had more green, and the solvent control strip was entirely green.

Example 7

A repeat of Example 6 was performed using different amounts of NaOH added to the indicator solution to treat the paper. Results indicated that using 0.02N NaOH produced a differentiated yellow front on the strips that traveled progressively higher on the strip as the EHA concentration increased. Each test was run until the solvent front reached the same point in the same amount of time. The solvent traveled 3.4 cm. Full strength EHA traveled 1.5 cm, 50% traveled 0.9 cm, 25% traveled 0.5 cm and the solvent had no yellow. Colors were read and recorded immediately as the indicator started to fade to yellow in all cases in about an hour.

Example 8

Additional substrates were evaluated for use as solid phase indicators. The 0.28% BTB/0.02N NaOH indicator from above was used to treat strips of acid free sketch paper and drawing paper. The result produced very distinct color changes from green/blue to bright yellow, but these papers were found to react with the heat laminating process and did not react with the EHA after laminating. The use of different laminating material or a cold laminating process may provide solid phase indicators that produce distinct color changes with minimal effects from the lamination process.

Example 9

To evaluate another substrate, thin strips (1.25 cm by 0.5 cm by 0.1 cm) of 5 micron sintered ultra high molecular weight polyethylene (UHMW PE) were treated with 0.28% BTB/0.02N NaOH alcoholic indicator solution. 1 drop of EHA standard from above was added to each strip and produced a bright yellow spot. The EHA-free 25/75 solvent did not change the color of the strip.

Two drops of the 0.28% BTB/0.02N indicator solution were added to the center of a thin strip of the sintered PE and allowed to dry. The end of the strip was dipped in the EHA in 25/75 standard from above and allowed to wick up the strip. The dot of blue turned bright yellow. A repeat experiment using the lower EHA concentrations produced commensurate amounts of green on the dot, with the solvent advancing the dot and turning it to a blue streak, evident to the eye.

Those skilled in the art will recognize, or be able to ascertain using no more than routine experimentation, many equivalents to the specific embodiments of the invention described herein. Such equivalents are intended to be encompassed by the following claims.

All references disclosed herein, including patent documents, are incorporated by reference in their entirety.

What is claimed is:

1. A method for identifying the quantity of a resident species present in a sample of an aqueous coolant, the method comprising the steps of:
   (a) obtaining a coolant sample of a measured quantity, wherein the coolant is an aqueous coolant;
   (b) contacting the coolant sample with an inorganic acid to protonate a resident species contained in the coolant sample;
   (c) mixing the contacted coolant sample of (b) with a quantity of an organic extraction solvent in which the protonated resident species is soluble, solubilizing the protonated resident species in the organic extraction solvent, and allowing the resulting mixture to separate into phases comprising at least an organic layer;
   (d) contacting the protonated resident species of a portion of the organic layer with a solid phase pH indicator; and
   (e) observing the length of the solid phase pH indicator that is subjected to a color change and comparing it to the length that the solvent has traveled on the solid phase pH indicator.

2. The method of claim 1 wherein the resident species is an organic acid.

3. The method of claim 2 wherein the solid phase pH indicator comprises a porous substrate, a pH indicator and a base.

\* \* \* \* \*